United States Patent [19]

Sato et al.

[11] Patent Number: 5,004,349
[45] Date of Patent: Apr. 2, 1991

[54] LIGHTING APPARATUS AND COLOR MEASURING APPARATUS USING THE SAME

[75] Inventors: Tsuyoshi Sato, Oita; Masahito Inaba; Naoya Takata, both of Osaka, all of Japan

[73] Assignee: Minolta Camera Kabushiki Kaisha, Osaka, Japan

[21] Appl. No.: 333,318

[22] Filed: Apr. 4, 1989

[30] Foreign Application Priority Data

Apr. 5, 1988 [JP] Japan .................................. 63-86173
Aug. 22, 1988 [JP] Japan ................................ 63-207816

[51] Int. Cl.$^5$ .......................... G01J 3/46; H05B 37/02
[52] U.S. Cl. .................................. 356/402; 315/151; 356/407; 356/419
[58] Field of Search ....................... 315/151, 293, 149; 355/38; 356/402, 407, 414, 416, 418, 419

[56] References Cited

U.S. PATENT DOCUMENTS 4,377,774 3/1983 Hosomizu ...................... 315/241 P
4,449,821 5/1984 Lee ....................................... 356/319
4,485,336 1/1984 Yoshiyama ...................... 315/241 P

FOREIGN PATENT DOCUMENTS 6150125 3/1986 Japan .
6150126 3/1986 Japan .
62284226 12/1987 Japan .

Primary Examiner—F. L. Evans
Assistant Examiner—K. P. Hantis
Attorney, Agent, or Firm—Price, Gess & Ubell

[57] ABSTRACT

A color measuring apparatus for measuring the color of a sample has a light source measuring section for detecting color temperature of light coming from a light source without passing through or being reflected by the sample. Relationship between a plurality of color temperatures and a plurality of emission time periods of the light source is stored in a memory. A microcomputer compares each of detected color temperatures with a predetermined value and determines a certain time period on the basis of both the relationship stored in the memory and a comparison result. A lighting circuit energizes the light source during the time period determined by the computer so that the light source keeps lighting the sample. A sample measuring section detects light coming from the sample and the microcomputer measures a color of the sample.

14 Claims, 24 Drawing Sheets

Fig. 3(a)
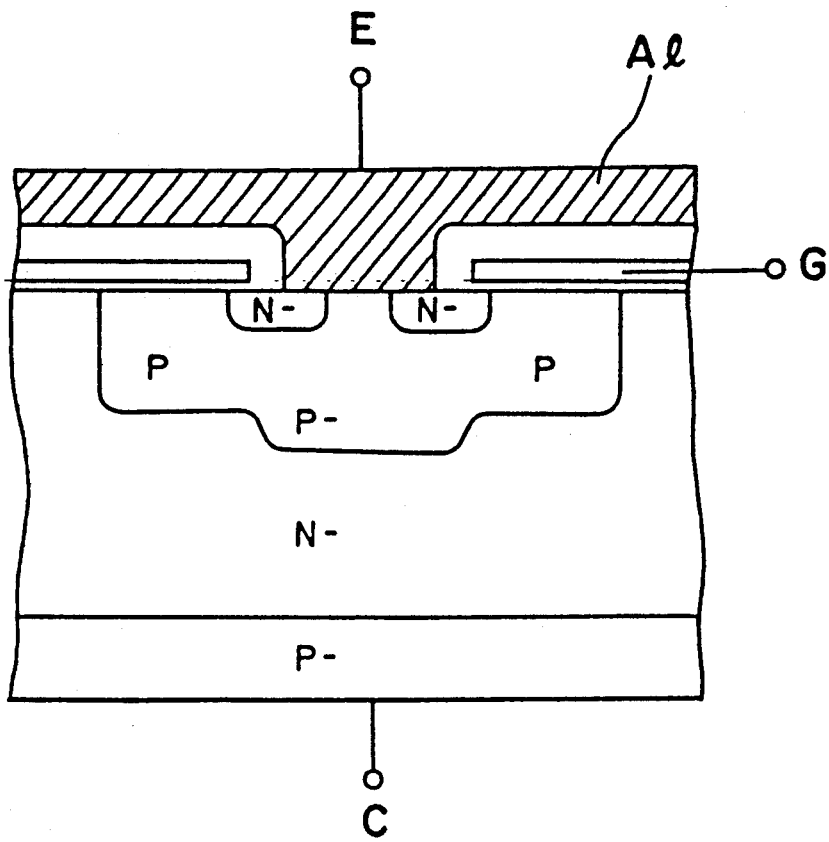
Fig. 3(b)
Fig. 3(c)
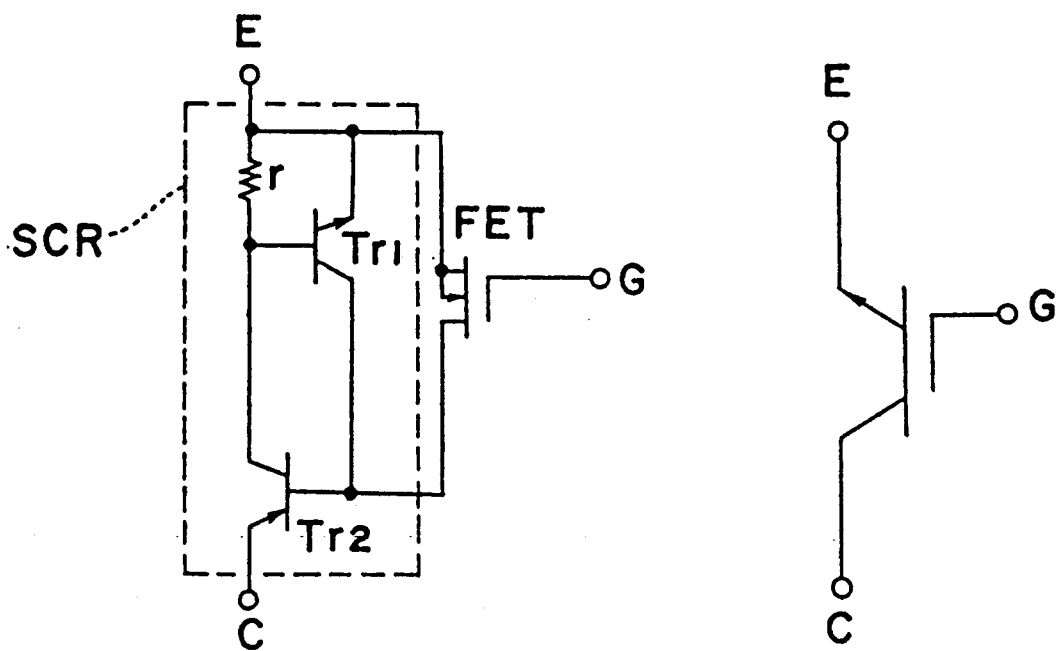

LIGHTING APPARATUS AND COLOR MEASURING APPARATUS USING THE SAME

BACKGROUND OF THE INVENTION

The present invention relates to a lighting apparatus and a color measuring apparatus capable of adjusting the color temperature of a light source.

An example of a known lighting apparatus is shown in FIG. 16. The known lighting apparatus is provided with a main capacitor C1 which holds electric charge for a flash tube Xe; a DC power supply 1 serving as a power supply circuit block which charges the main capacitor C1 to a predetermined voltage; a reverse current preventing diode D1 which prevents the reverse flow of the electric charge from the main capacitor C1; a thyristor SCR2 serving as a switch element provided in a main discharge loop of the main capacitor C1; a commutation capacitor C2 which holds electric charge for forcing the electric current flowing through the main discharge loop to commutate; a thyristor SCR1 serving as a switch for discharging the commutation capacitor C2; resistors r1 and r2 for charging the commutation capacitor C2 at an initial level prior to light emission of the flash tube Xe; a trigger circuit Tr serving as a circuit for energizing the flash tube Xe; and a control circuit 2 which controls the start and forced stop of the light emission of the flash tube Xe.

In the lighting apparatus having the above-described construction, when the thyristor SCR2 is turned on when receiving a light emission start signal applied from the control circuit 2, simultaneously the trigger circuit Tr starts to operate. Consequently, the flash tube Xe starts emitting a light. When a time t1 shown in FIG. 17 is passed, the thyristor SCR1 is turned on in response to a light emission stop signal applied thereto from the control circuit 2. As a result, the electric charge in the commutation capacitor C2 reverse-biases the thyristor SCR2 between the anode and cathode thereof during the discharge time period T2 of the commutation capacitor C2 and the thyristor SCR2 is turned off. When a residual voltage of the main capacitor C1 becomes the same as the voltage charged on the commutation capacitor C2, the light emission of the flash tube Xe stops.

Thus, according to the above-described known lighting apparatus, in order to stop the light emission of the flash tube Xe, the thyristor SCR2 is reverse-biased between the anode and cathode thereof and turned off by turning on the thyristor SCR1 according to the light emission stop signal applied thereto from the control circuit 2. The flash tube Xe stops emitting a light when the residual voltage of the main capacitor C1 becomes balanced with the voltage charged on the commutation capacitor C2. For this reason, even after the thyristor SCR2 is turned off, electric current flows in the main discharge loop through the flash tube Xe, the commutation capacitor C2, and the thyristor SCR1. Therefore, an over-emission occurs as shown in FIG. 17. The over-emission period of the flash tube Xe greatly depends on the initial condition of the commutation capacitor C2, the temperature characteristics of the parts of the respective circuits and the light emission period. Accordingly, the over-emission period of the flash tube Xe varies every time as shown in FIG. 17.

That is, according to the above-described lighting apparatus, every time light is emitted, the over-emission period varies and as such, light emission quantities differ. Accordingly, it is difficult to make the color temperature of the light emitted by the flash tube Xe constant. It is also difficult to control the initial conditions and temperature characteristics of the main capacitor C1 and the commutation capacitor C2 so as to get a same over-emission period at every emission, namely, to get a same light emission quantity at every emission.

In addition, when reflectance or transmittance is measured based on light reflected by a sample or light which has passed therethrough by using the above-described lighting apparatus, S/N ratio is not preferable in a low reflectance wavelength band or a low transmittance wavelength band.

The color temperature of a light source is varied by discharged electric current and the temperature of a discharge tube. The discharged electric current can be made to be constant by appropriately constructing the power supply. But the temperature of the discharge tube rises as a result of repeated discharges and also rises if it repeats light emissions in a relatively short period. Therefore, it is difficult to keep the color temperature of the light source constant when the discharge tube is used as the light source.

SUMMARY OF THE INVENTION

It is therefore an object of the present invention to provide a lighting apparatus for using in a color measuring apparatus in which the color temperature of a light source is not varied due to the response delay of a lighting control circuit and the temperature characteristics of circuit parts.

It is another object of the present invention to provide a lighting apparatus in which a discharge tube is used as a light source and the variation of the color temperature of the light source does not occur when a plurality of measurements can be performed in a short period of time.

It is another object of the present invention to improve the S/N (signal to noise) ratio in a color measurement of a sample by using a color measuring apparatus which has a lighting apparatus and spectral light receiving elements which detect spectral light amounts of light coming from the sample illuminated by the lighting apparatus, wherein, when it is judged on the basis of outputs of the spectral light receiving elements that a sample to be measured has wavelength band of a low spectral reflectance or low spectral transmittance, at least one of an electric charge voltage of a main capacitor, a pulse width of a gate pulse signal, and pulse voltage of the gate pulse signal is controlled so as to control a color temperature of an emitted light, whereby light quantities in the low reflectance or transmittance wavelength band of the emission light are increased, thus realizing the improvement of the S/N.

A color measuring apparatus in this invention operates as follows.

Means for energizing a light source formed of a discharge tube, for example, stores discharge energy in a capacitor and the electric charge of the capacitor is discharged through the discharge tube as light emission by applying a trigger voltage to the discharge tube and the light emission of the discharge tube is stopped by interrupting the flow of electric current to the discharge tube. When a discharge time period of the discharge tube is changed, a color temperature of the light emitted thereby changes. For example, if the discharge time period is long, the color temperature of the emitted light becomes low. The relationship between the emission period and the color temperature depends on the character of the discharge tubes. This relationship is obtained by carrying out calibration measurement in respective light measuring apparatuses and the result can be stored in a memory. The color temperature of light emitted by the discharge tube also differs according to the temperature of the discharge tube. For example, the higher the temperature of the discharge tube is, the lower the color temperature of the emitted light becomes. This relationship can also be stored in the memory. Needless to say, the temperature of the discharge tube rises due to a discharge. Therefore, the color temperature is lower when the discharge time period is long. If discharge is carried out at a considerable interval of time from the previous discharge, the temperature of the discharge tube becomes to a room temperature. But when light emissions are repeated, the temperature of the discharge tube gradually rises because a light is newly emitted before the temperature of the discharge tube which has risen due to the previous light emission lowers down to the room temperature. Thus, the temperature of the discharge tube rises gradually while light emissions are repeated. According to the present invention, the relationship between the light emission time period and the color temperature of the previous light emission are stored. Therefore, if the color temperature of the previous light emission is lower than a desired value, the light emission time period is considered to have been too long, and the light emission time period of a next time is controlled to be shorter than the previous light emission time period. A time period to be shortened is determined by finding a light emission time period against a unit of difference of color temperature based on a table indicating the relationship between the emission time period and the color temperature. If an interval between the previous light emission time and the current light emission time is considerably long, the current light emission can be carried out under predetermined target light emission conditions. Accordingly, the light emission time period is controlled to be desired value.

The light emission time period is controlled more accurately by detecting a temperature of the discharge tube, because this method can control the light emission time period more directly than the above method using the color temperature obtained at the previous light emission.

The lighting apparatus as another invention operates as follows: The power supply circuit charges the capacitor to a predetermined voltage. The computing means obtains a light emission time period from a table indicating the relationship between a plurality of emission time periods of the flash tube and a plurality of color temperatures of the flash tube stored in the memory based on the designated color temperature. The control means energizes the flash tube for a time based on the obtained emission time period. As a result, the charge stored in the capacitor is discharged for a predetermined time period, which leads to the light emission of the flash tube.

Since the light emission time period of the flash tube is controlled by the control means, the over-emission quantity can be reduced, and further, made to be constant and the color temperature can also be controlled to be constant.

BRIEF DESCRIPTION OF THE DRAWINGS

The present invention will become more fully understood from the detailed description given below and the accompanying drawings which are given by way of illustration only, and thus are not limitative of the present invention, and wherein:

FIG. 3(a) is a view showing the construction of an insulated gate bipolar transistor (IGBT) for use in the embodiment;

FIG. 3(b) is an equivalent circuit diagram of the IGBT of FIG. (3a);

FIG. 3(c) is a view showing the elements of the IGBT;

DETAILED DESCRIPTION OF PREFERRED EMBODIMENTS

Figure 1:
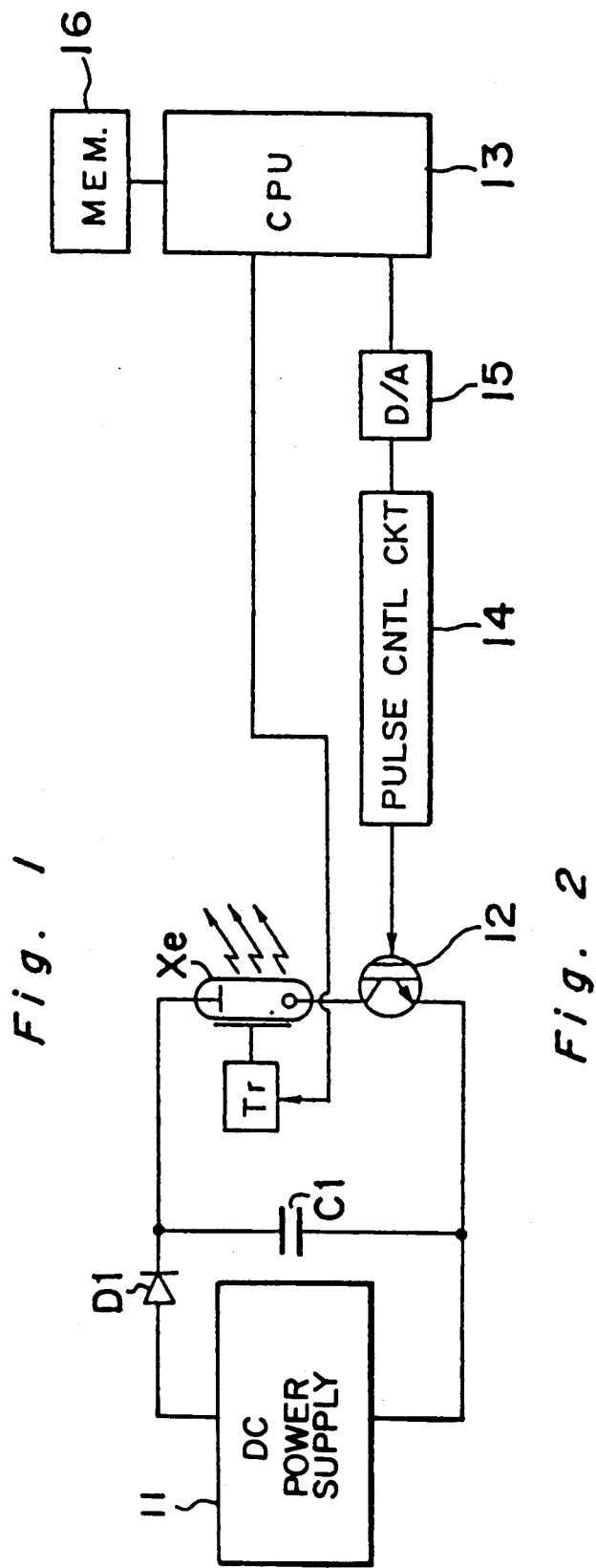
FIG. 1 is a block diagram of one embodiment of a flashlight emission apparatus as a lighting apparatus in accordance with the present invention.

Referring to FIG. 1 showing a block diagram of a flashlight emission apparatus as an embodiment of a lighting apparatus comprising a insulated-gate bipolar transistor (hereinafter referred to as IGBT) 12, a main capacitor C1 is a capacitor which holds electric charge to be used by a flash tube Xe, a DC power supply 11 is a power supply block for charging the main capacitor C1 at a constant voltage, a diode D1 is for preventing the reverse flow of the electric charge of the main capacitor, and a trigger circuit Tr is a circuit for energizing the flash tube Xe.

The IGBT 12 is a switch element provided in a main discharge loop of the main capacitor C1. The flash light emission apparatus further comprises a CPU (central processing unit) 13 which outputs an emission control signal for controlling the start and forced stop of the emission of the flash tube Xe, a pulse control circuit 14 which outputs to a gate of the IGBT 12 a gate pulse signal having a pulse width and a pulse voltage in accordance with the emission control signal inputted thereto from the CPU 13 through a D/A converter 15, and a memory 16 which stores a table indicating the correlation between the flashlight emission time and the color temperature of the flash tube.

The detailed description of the IGBT 12 will be made hereinbelow. FIG. 3(a) shows the fundamental construction of the IGBT 12; FIG. 3(b), the equivalent circuit thereof; and FIG. 3(c), symbols of the elements thereof. As shown in FIG. 3(b), the IGBT 12 comprises the combination of a MOSFET and a thyristor SCR having a PNPN structure shown by a dotted line which forms a block. As shown in FIG. 3(b), in a PNP transistor Tr1, the base and the emitter are connected through a resistor 'r' so that the thyristor SCR is not latched up, i.e., so that electric current does not keep flowing when a gate signal is removed. When a voltage is applied to the gate G of the IGBT 12, the MOSFET is turned on. As a result, electric current flows from the collector C to the emitter E of the IGBT 12 through the thyristor SCR.

Figure 3D:
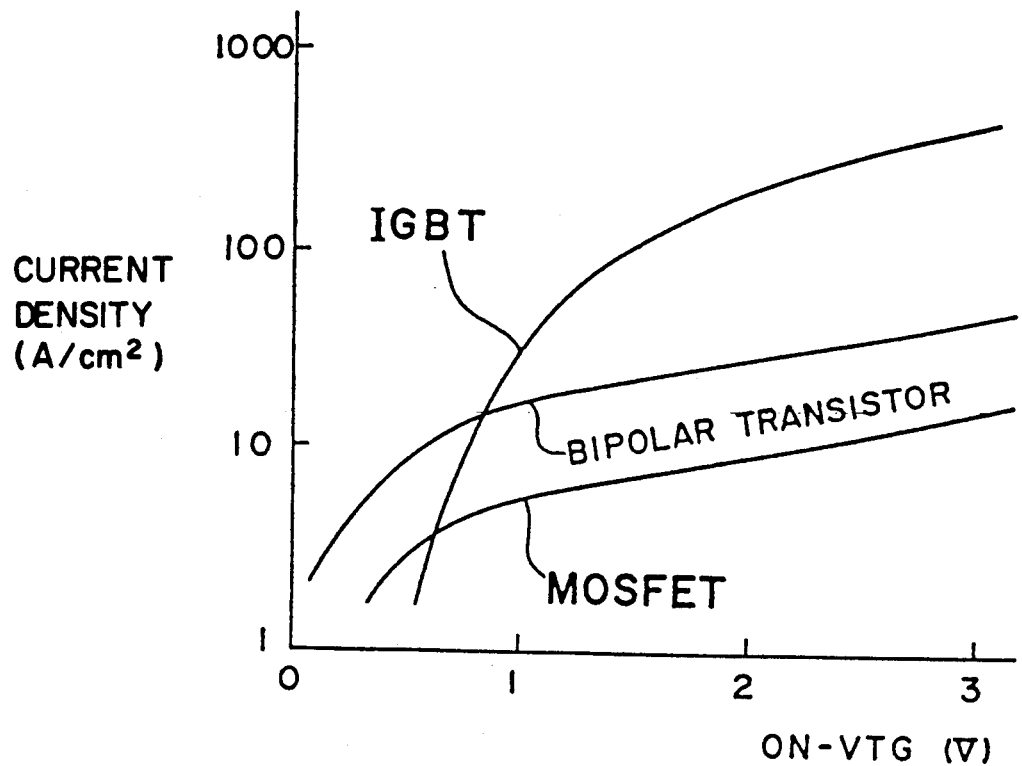
FIG. 3(d) is a graph showing the current density of the IGBT.
Figure 3E:
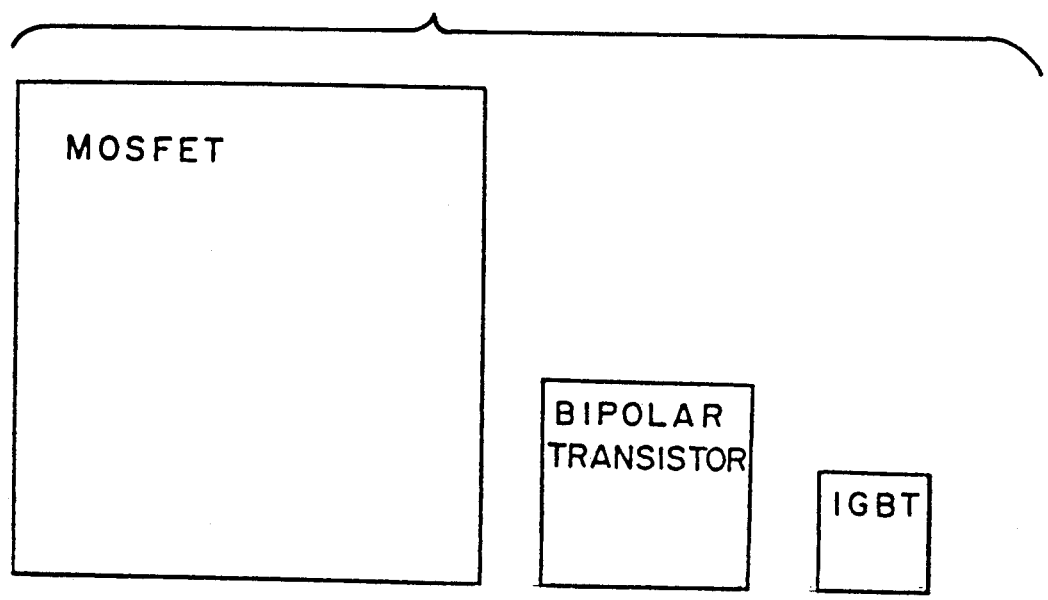
FIG. 3(e) is a view showing the proportion of areas of the elements of the IGBT.

As apparent from FIG. 3(a), the basic construction of the IGBT 12 is similar to that of the MOSFET. That is, similarly to the MOSFET, since the IGBT 12 is operated by voltage, the control circuit thereof can be of a small size, and further, the IGBT is turned on or off quickly. As shown in FIG. 3(d), since the IGBT can have a large current density when compared with a bipolar transistor (Darlington connection) and the MOSFET, the dimension of the IGBT 12 can be smaller than those of the bipolar transistor and the MOSFET. FIG. 3(e) shows the difference among the areas of the chips of elements necessary for setting the ON-voltage to 3 V when electric current of 25 amperes flows, the elements being the MOSFET, the bipolar transistor, and the IGBT 12.

Since the switching time of the IGBT 12, namely, its turn-on time is approximately 0.4 $\mu$s and its turn-off time is approximately 1.0 $\mu$s, its switching time is much shorter than that of the known flashlight emission apparatus in which a thyristor is employed. Therefore, a flashlight emission apparatus in which the IGBT 12 is used enables a high speed switching.

Next, the color temperature of a light emitted by the flash tube Xe will be described hereinbelow. The color temperature of an emission light of the flash tube Xe depends on the density of the current which flows through the flash tube Xe when the flashlight is emitted.

The density of the current is determined by both a circuit impedance of a discharge loop including the flash tube Xe and a voltage applied to the electrodes of the flash tube Xe when a flashlight is emitted. The impedance of a flash tube Xe is determined by the pressure of a gas included therein and the distance between the electrodes thereof and accordingly, different flash tubes Xe have their own impedances. The density of the flashlight emission current is controlled either by adjusting the voltages applied to the electrodes thereof or inserting an element capable of controlling its impedance into the discharge loop in series separately from the flash tube Xe so as to directly control the flashlight emission current.

Figure 4:
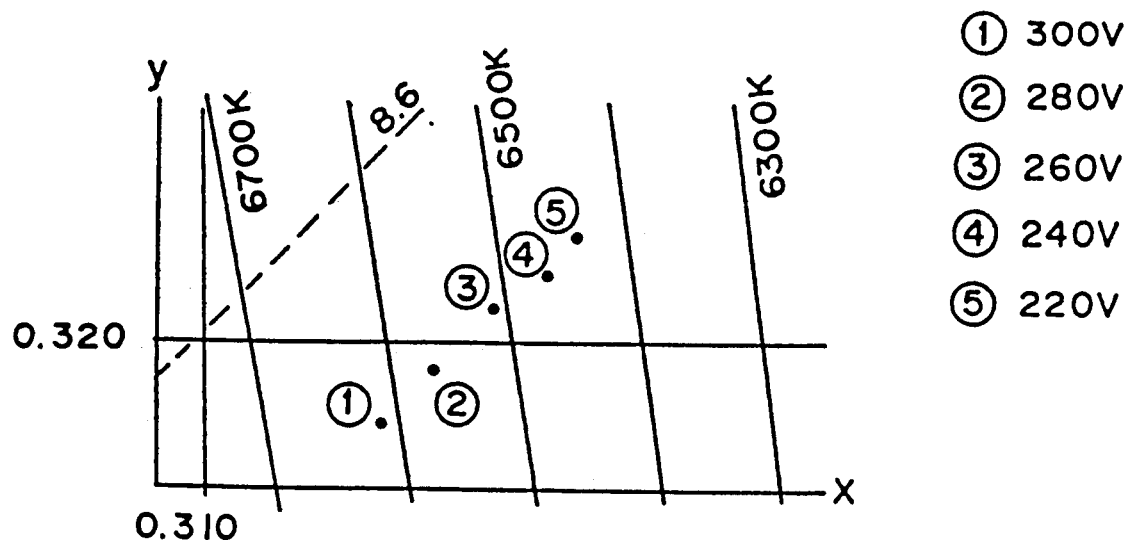
FIG. 4 is an xy chromaticity diagram showing the relationship between the charge voltage of a main capacitor and the color temperature of flash tube.

FIG. 4 shows a change in the color temperature of the light emitted from the flash tube Xe plotted on an xy chromatic diagram of CIE standards. In this case, the main capacitor C1 of 608 $\mu$F is used and the charge voltage is varied from 300 V to 220 V. As apparent from FIG. 4, the color temperature becomes higher with the increase of the charge voltage of the main capacitor C1.

Figure 5:
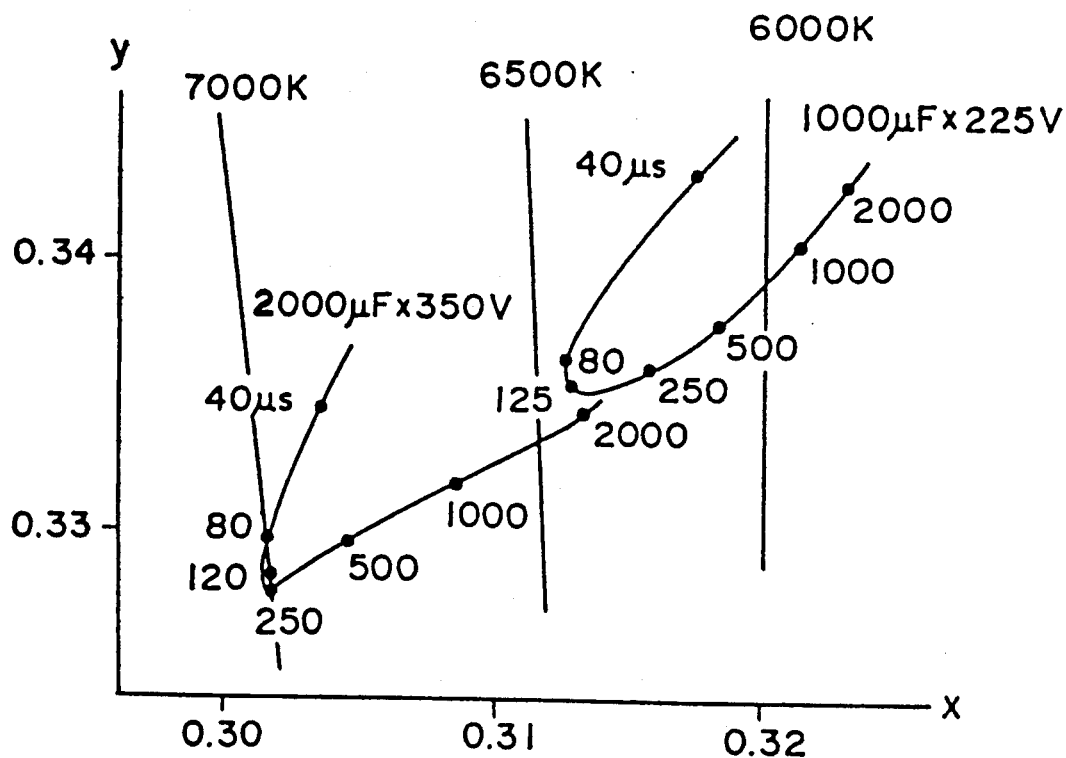
FIG. 5 is an xy chromaticity diagram showing the relationship between the flashlight emission time and color temperature of the flash tube.

The color temperature also depends on the flashlight emission time. FIG. 5 shows a change in the color temperature of the light emitted from the flash tube Xe plotted on an xy chromatic diagram when the flashlight emission time is changed in the range from 40 $\mu$s through 2000 $\mu$s. In this case, a main capacitor C1 of 2000 $\mu$F and the main capacitor of 1000 $\mu$F are used and the charge voltages are 350 V and 225 V, respectively.

The color temperature of a light emitted from the flash tube Xe is changed by the voltage applied to the electrodes thereof while it is emitting the flashlight. More specifically, if the charge voltage to the flash tube Xe is high, the color temperature becomes high. After a rise-time of the flashlight emission has passed, the voltage applied to the electrodes of the flash tube Xe is reduced with the elapse of time. As a result, the color temperature falls.

The flashlight emission apparatus having the above-described construction operates as follows: Referring to FIG. 1, the emission control signal of a digital form outputted from the CPU 13 is converted to an analog form by the D/A converter 15, then inputted to the pulse control circuit 14. In response to the emission control signal outputted from the CPU 13, the pulse control circuit 14 outputs a gate pulse signal having a predetermined pulse width or a predetermined pulse voltage, which is described later.

Thereafter, the gate pulse signal is applied to the gate of the IGBT 12. As a result, the IGBT 12 is turned on. In synchronization with the turn-on of the IGBT 12, the trigger circuit Tr is operated by a signal applied thereto from the CPU 13, which allows the flash tube Xe to emit light. When a time t1 corresponding to the pulse width of the gate pulse signal elapses after the flash tube Xe starts to emit, the gate pulse signal is not applied to the gate of the IGBT 12. As a result, the IGBT 12 is turned off and the flash tube Xe stops emitting.

Figure 2:
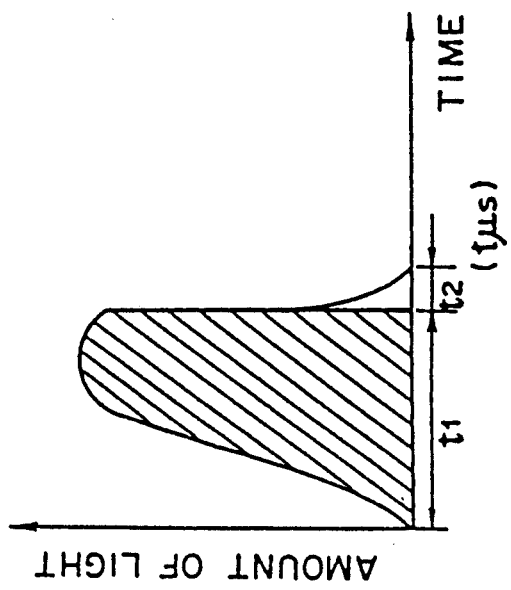
FIG. 2 is a graph showing the relationship between flashlight emission times and light amounts.
Figure 17:
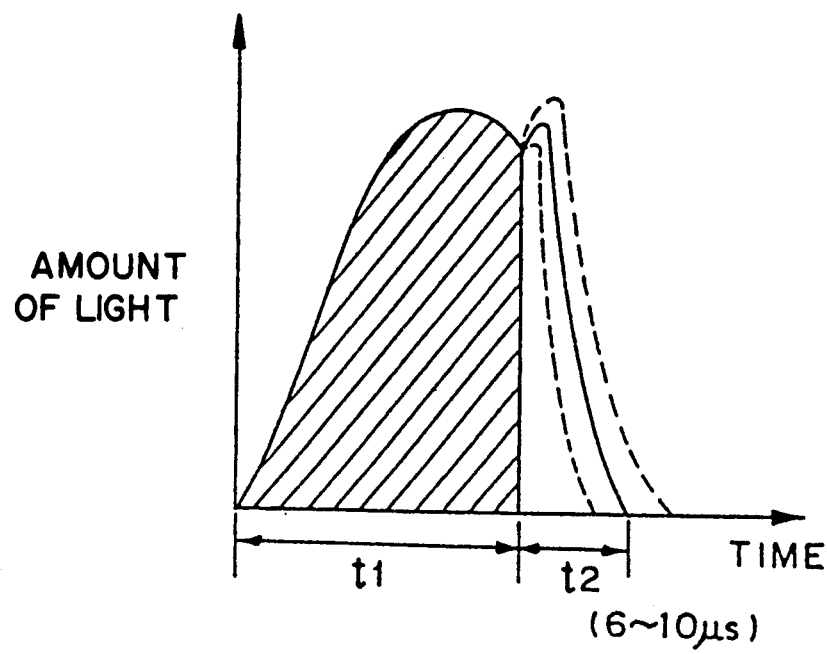
FIG. 17 is a graph showing the relationship between the flashlight emission times and the light amounts in the known flashlight emission apparatus.

At this time, the flash tube Xe stops the emission in a very short time as described above. Therefore, as shown in FIG. 2, an amount of overemitted flashlight, namely the amount of the flashlight emitted after the flash tube Xe is turned off, is much smaller than that of the known flashlight emission apparatus as shown in FIG. 17 in which the flashlight emission is stopped by turning off a thyristor by means of a commutation capacitor. Furthermore, there is trivial unevenness in the amounts of overemitted flashlights.

The method for controlling the color temperature of the light emitted by the flashlight emission apparatus is described on the case in which the flashlight emission apparatus emits a flashlight only once.

As shown in FIG. 5, the color temperature of the light emitted therefrom varies according to a flashlight emission time. Accordingly, if other conditions are the same, the color temperature becomes constant by setting the flashlight emission time to be constant. For example, if a voltage of 350 V is applied to the main capacitor C1 of 2000 $\mu$F and the flashlight emission time is set to approximately 1700 $\mu$s, a flashlight is emitted from a D65 light source having the color temperature of 6500 K. The D65 light source conforms to a CIE standard illuminant. In this case, the turn-off time of the known flashlight emission apparatus in which the thyristor is used varies in the range from 6 to 10 $\mu$s as shown in FIG. 17, while as shown in FIG. 2, the turn-off time of the flashlight emission apparatus of this embodiment in which the IGBT 12 is used is as short as 1 $\mu$s. Accordingly, the flashlight emission time can be controlled with a considerably high accuracy, so that the color temperature of the light emitted by the flash tube Xe can be accurately controlled.

The relationship between the color temperature and the flashlight emission time is varied according to flash tubes as shown in FIG. 5. Considering this, the correlation between the color temperature and the flashlight emission time of the flash tube Xe is examined in advance so that a table indicating the correlation therebetween is stored in the memory 16. When a flashlight of a certain color temperature is emitted, the CPU 13 reads a flashlight emission time corresponding to the color temperature from the memory 16, thus outputting the emission control signal corresponding to the read flashlight emission time to the D/A converter 15. The D/A converter 15 performs a D/A conversion of the emission control signal and outputs the D/A converted signal to the pulse control circuit 14. Subsequently, the pulse control circuit 14 outputs to the gate of the IGBT 12 the gate pulse signal of the pulse width corresponding, for example, to t1 in FIG. 2 based on the emission control signal outputted from the CPU 13. As a result, the IGBT 12 operates for the flashlight emission time t1 set by the CPU 13. After the IGBT 12 operates, the IGBT 12 turns off in the time of t2 as described above. Therefore, the total amount of the flashlight emission time of the flash tube Xe comes to exactly t1+t2. Thus, according to this embodiment, the color temperature of the light emitted from the flash tube Xe can be controlled to be constant.

The operation described above is concerned with the case in which a flashlight is emitted once, but actually the flashlight emission apparatus performs the light emission several times and the number of flashlight emissions is controlled, whereby the amount of lights from the flashlight emission apparatus is controlled.

Figure 6:
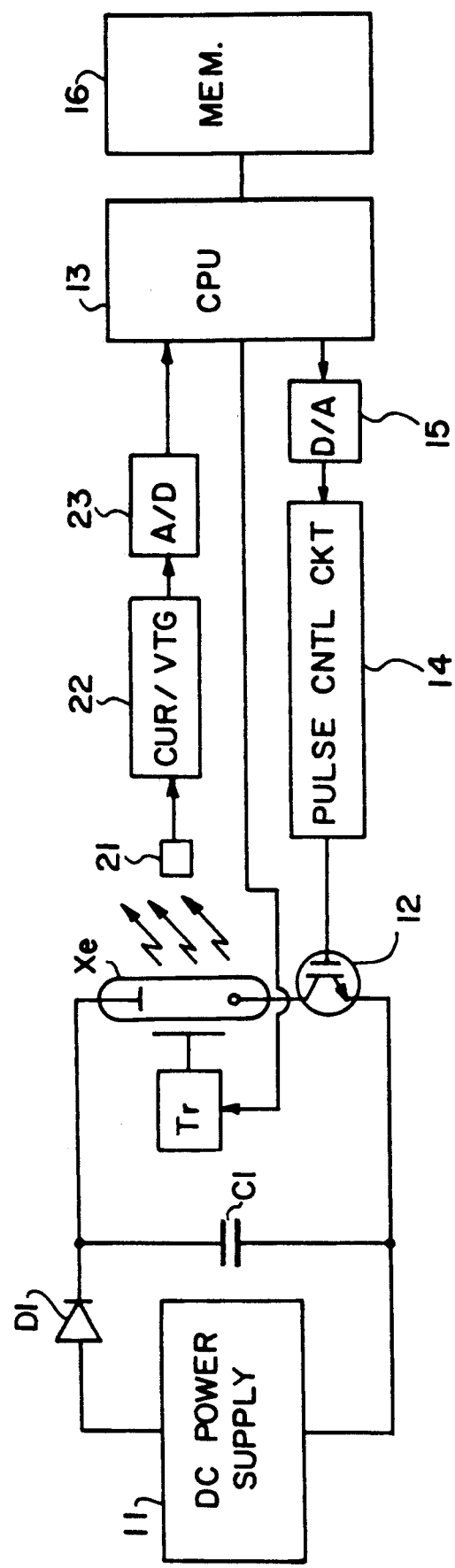
FIG. 6 is a block diagram of a flashlight emission apparatus capable of controlling an emission amount by controlling the number of emissions of the flash tube.

FIG. 6 shows a block diagram of a flashlight emission apparatus capable of controlling the emission amount. A photosensor 21 detects the emission amount of the flash tube Xe and outputs a current indicative of the emission amount. The signal outputted from the photosensor 21 is converted into a voltage by a current/voltage converter 22. The voltage is A/D-converted by an A/D converter 23, then the A/D converted signal is applied to the CPU 13.

Based on the signal applied from the A/D converter 23, the CPU 13 accumulates or integrates the emission amount of the xenon flash tube detected by the photosensor 21 by means of an emission amount accumulating means, and compares the accumulated or integrated emission amount with a predetermined emission amount by an emission amount comparing means in the CPU 13. If the accumulated emission amount is less than the predetermined emission amount, the CPU 13 outputs the subsequent gate pulse signals to the gate of the IGBT 12 at shorter intervals of time to increase the emission amount of the flash tube Xe. When the accumulated emission amount becomes equal to the predetermined emission amount, the CPU 13 stops the output of the emission control signal to the D/A converter 15.

Since the IGBT 12 is used as a switching element, the flashlight emission apparatus stops the emission of a flashlight in a short time. Accordingly, the flashlight emission apparatus emits a flashlight in a constant amount every time it emits the flashlight, i.e., the total emission amount of the flashlight emission apparatus can be effectively controlled.

According to the above-described embodiment, every time a flashlight is emitted, an accumulated emission amount and the predetermined emission amount are compared with each other. But the emission amount may be controlled as follows: The CPU 13 calculates the number N of emissions of the flash tube Xe necessary for obtaining the predetermined emission amount based on an emission amount of a first time emission, then, outputs emission control signals in the number of N-1 times to the D/A converter 15. After N times emissions, if the accumulated or integrated emission amount of N emissions is less than the predetermined emission amount, the CPU 13 calculates again the number of residual emissions necessary for obtaining the predetermined emission amount, and outputs the emission control signal to the D/A converter 15 so that the flash tube Xe further emits flashlights.

As described hereinabove, when flashlights are repeatedly emitted to obtain the predetermined emission amount, the color temperature of the light emitted by the flash tube Xe is slightly fluctuated at each emission due to the change with the time of the DC power supply 11 or other factors. Then a control of the color temperature with a high accuracy is required.

Figure 7:
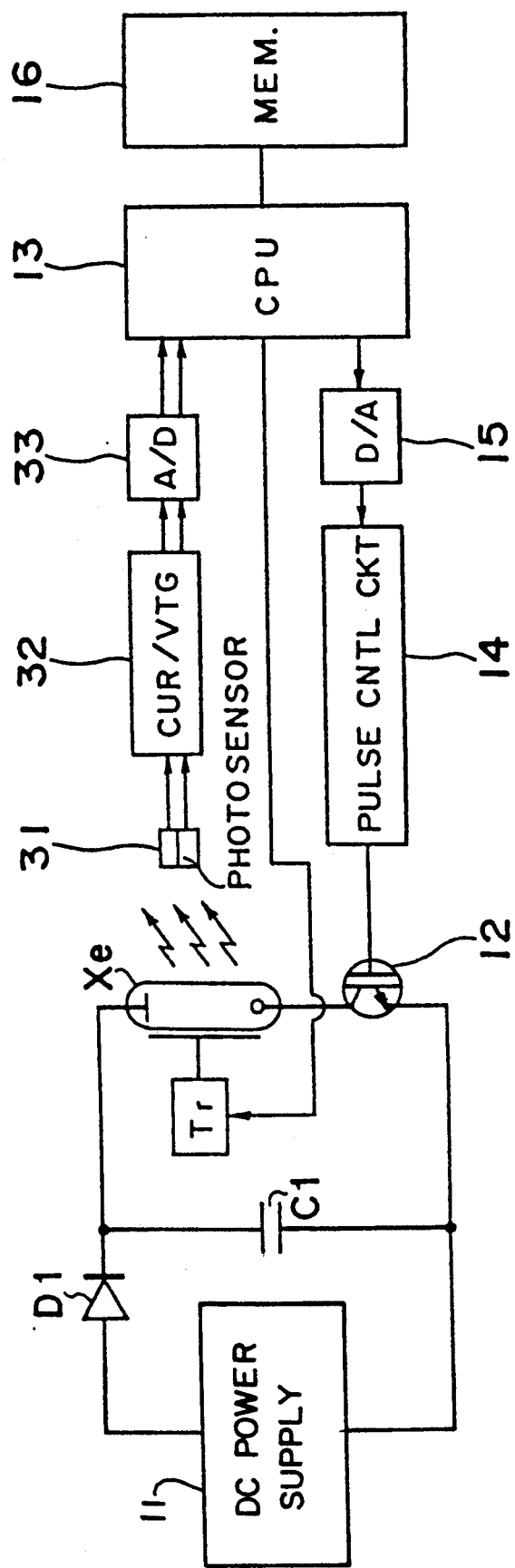
FIG. 7 is a block diagram of a flashlight emission apparatus as a lighting apparatus capable of controlling the color temperature of the light emitted by the flash tube as well as controlling emission amounts.

FIG. 7 is a block diagram of a flashlight emission apparatus capable of controlling the color temperature with a high accuracy in emitting flashlights successively. Photosensors 31 detect amounts of light components of the flashlight emitted by the flash tube Xe in at least two wavelength bands (two wavelengths in this embodiment). The memory 16 stores a correlation table showing the correlation between the difference between the measured color temperature of the light emitted by the flash tube Xe and the specified or designated color temperature and the flashlight emission time for compensating the color temperature difference.

The flashlight emission apparatus having the above-described construction operates as follows:

Signals of the photosensors 31 indicative of the emission light amounts in two wavelength bands are converted into voltages by a current/voltage converter 32 respectively and the converted signals are converted to a digital form by an A/D converter 33 to be inputted to the CPU 13.

On receipt of the two signals outputted from the A/D converter 33, the CPU 13 calculates the color temperature of the light emitted by the flash tube Xe to calculate the difference between the calculated color temperature and the specified color temperature by means of a color temperature difference calculating means in the CPU 13. Based on the color temperature difference, the CPU 13 finds a flashlight emission time for compensating the color temperature difference from the correlation table stored in the memory 16, thereby outputting emission control signals corresponding to the flashlight emission time to the D/A converter 15. In response to the emission control signals, the D/A converter 15 performs the D/A conversion of the emission control signal and outputs analog-form signals to the pulse control circuit 14. The pulse control circuit 14 outputs to the gate of the IGBT 12 a gate pulse signal with a pulse width corresponding to the flashlight emission time for compensating the color temperature difference. Accordingly, each of the subsequent flashlight emission times of the flash tube Xe is set to a flashlight emission time for compensating the color temperature difference. Thus, the color temperature of the light emitted by the flash tube Xe is set to the specified color temperature.

Thus, every time a flashlight is emitted by the flash tube Xe, the color temperature difference of the flashlight is measured to be corrected. Accordingly, the color temperature can be set to the specified color temperature. In this case, the color temperature of the illuminant is the average of the color temperatures of the N times emissions of the flash tube Xe. Therefore, fluctuation in the color temperature due to the above-described factors is averaged and the illuminant or light source becomes stable. Accordingly, the light emitted by the light source is stable.

In the above-described embodiment, the color temperature of the light emitted by the flash tube Xe is controlled by controlling the pulse width of the gate pulse signal outputted from the pulse control circuit 14. The color temperature will also be controlled by controlling the voltage of the DC power supply 11 as well. That is, as shown in FIG. 4, if other conditions are the same, the color temperature depends on the voltage applied to the flash tube Xe. Accordingly, the color temperature can be set to a specified value by controlling the voltage to be applied to the flash tube Xe, namely, by controlling the voltage of the DC power supply 11 to charge the main capacitor C1 at a specified voltage.

Figure 8:
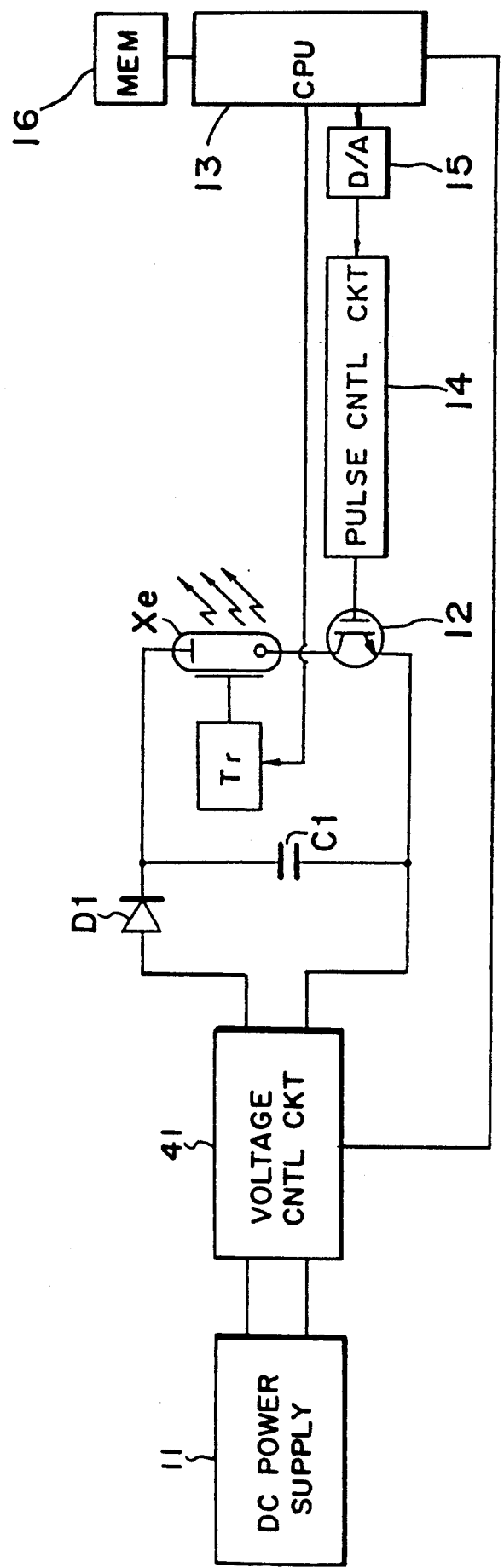
FIG. 8 is a block diagram of a modification of the flashlight emission apparatus of FIG. 1, wherein the voltage of the DC power supply can be controlled.
Figure 9:
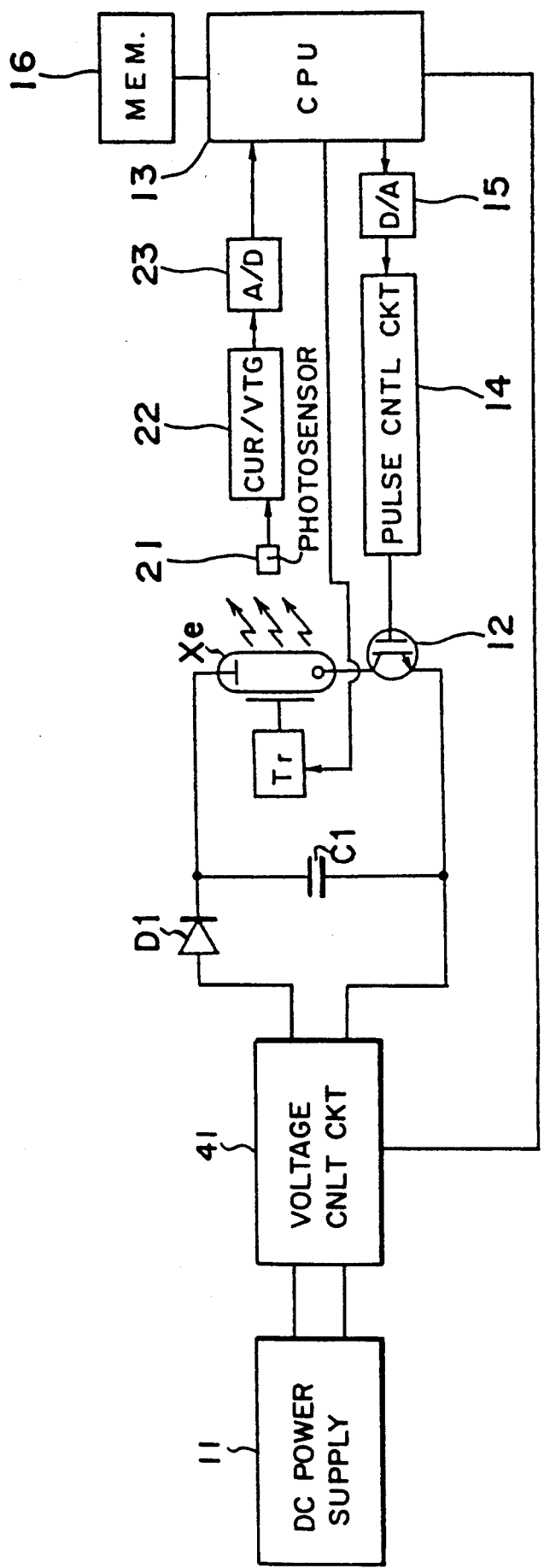
FIG. 9 is a block diagram of a modification of the flashlight emission apparatus of FIG. 6, wherein the voltage of the DC power supply can be changed.
Figure 10:
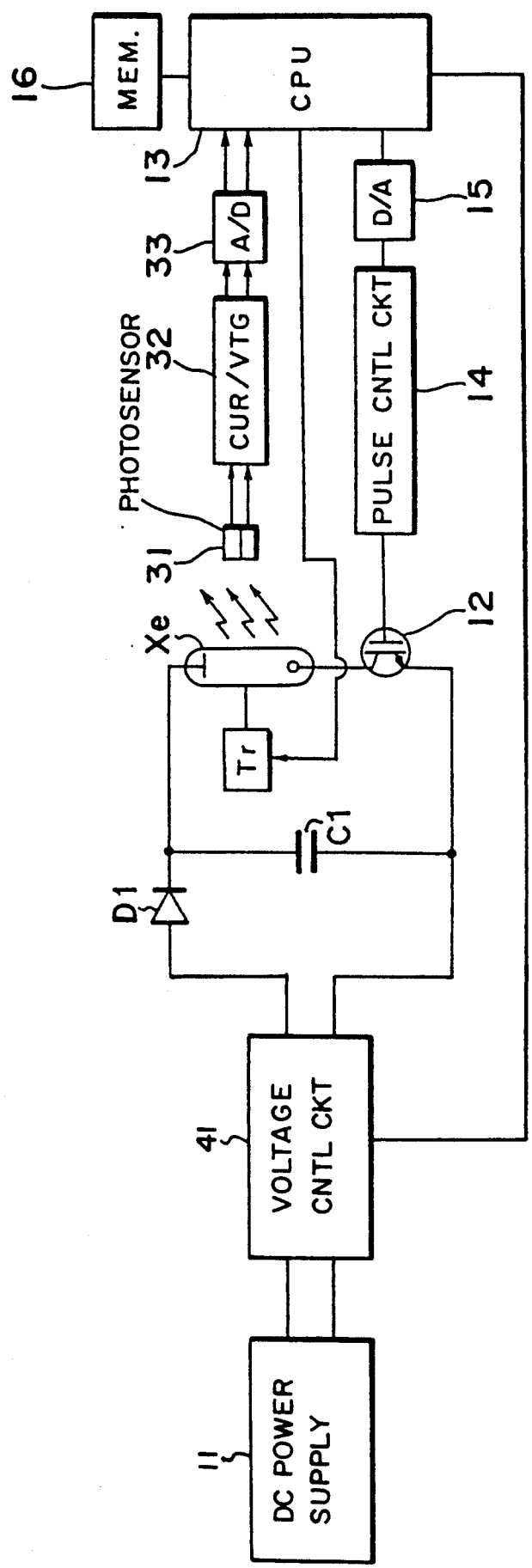
FIG. 10 is a block diagram of a modification of the flashlight emission apparatus of FIG. 7, wherein the voltage of the DC power supply can be changed.

FIG. 8 shows a block diagram of a modification of the flashlight emission apparatus of FIG. 1, wherein a voltage control circuit 41 is provided. FIG. 9 shows a block diagram of a modification of the flashlight emission apparatus of FIG. 6, wherein the voltage control circuit 41 is provided too. FIG. 10 shows a block diagram of a modification of the flashlight emission apparatus of FIG. 7, wherein the voltage control circuit 41 is provided too. According to each of the flashlight emission apparatuses shown in FIGS. 8, 9, and 10, a color temperature, namely, a voltage of the DC power supply 11 is set by the voltage control circuit 41 for controlling the color temperature generally and the pulse width of the gate pulse signal outputted from the pulse control circuit 14 for adjusting that accurately. Accordingly, the color temperature can be varied in a wide range with high accuracy.

Figure 11:
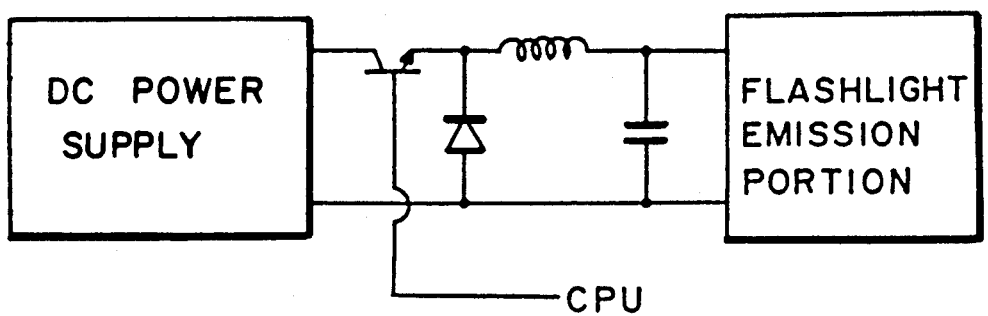
FIG. 11 is a circuit diagram of the voltage control circuits shown in FIGS. 8, 9, and 10.

The voltage control circuit 41 is, for example, a DC-DC converter as shown in FIG. 11 capable of controlling a voltage by a switching, which controls the voltage of the DC power supply 11 in response to "H" (high) and "L" (low) level signals outputted from the CPU 13.

Each of the above-described flashlight emission apparatuses is capable of controlling the color temperature of the light emitted by the flash tube Xe in a wide range by controlling the pulse width of the gate pulse signal, the voltage of the DC power supply 11.

Figure 12:
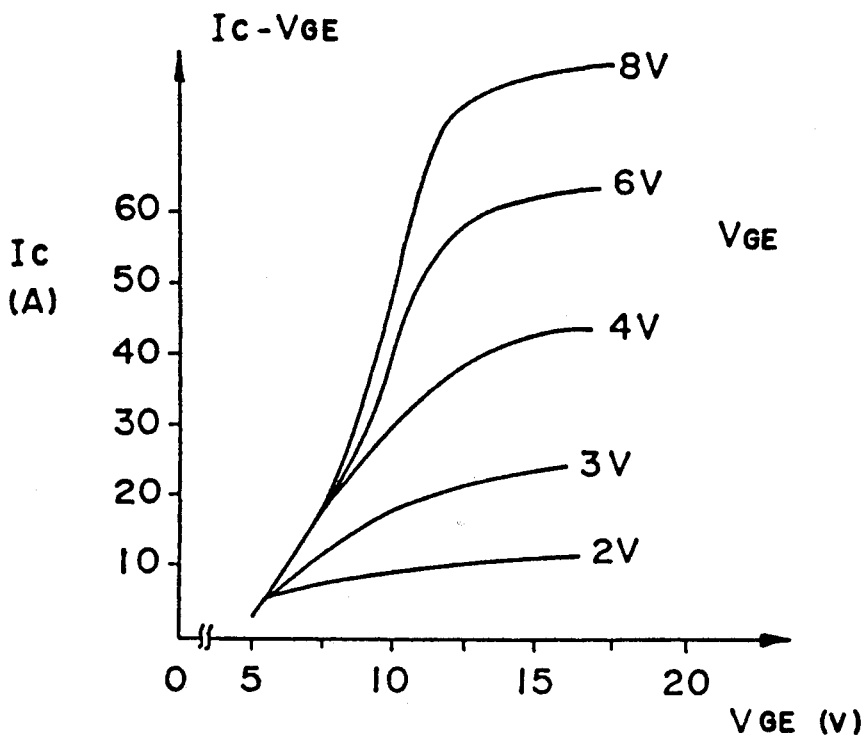
FIG. 12 is a graph showing the relationship between the current density of a flashlight emission current and the gate voltage of the IGBT.

It is possible to control the color temperature thereof with controlling the gate voltage obtained when the gate pulse signal is ON. That is, as shown in FIG. 12, a flashlight emission current (namely, collector current IC of the IGBT 12) depends on a gate voltage VGE of the IGBT 12, while the color temperature of the light emitted by the flash tube Xe depends on the density of the flashlight emission current which flows through the flash tube Xe when the flashlight is emitted. Accordingly, color temperature of the light emitted by the flash tube Xe can be controlled by the pulse voltage of the gate pulse signal outputted from the pulse control circuit 14.

Therefore, if the color temperature is set by the pulse voltage of the gate pulse signal generally and finely adjusted by the pulse width of the gate pulse signal, the color temperature of the light emitted by the flash tube Xe can be controlled in a wide range and with a high accuracy too.

Figure 13:
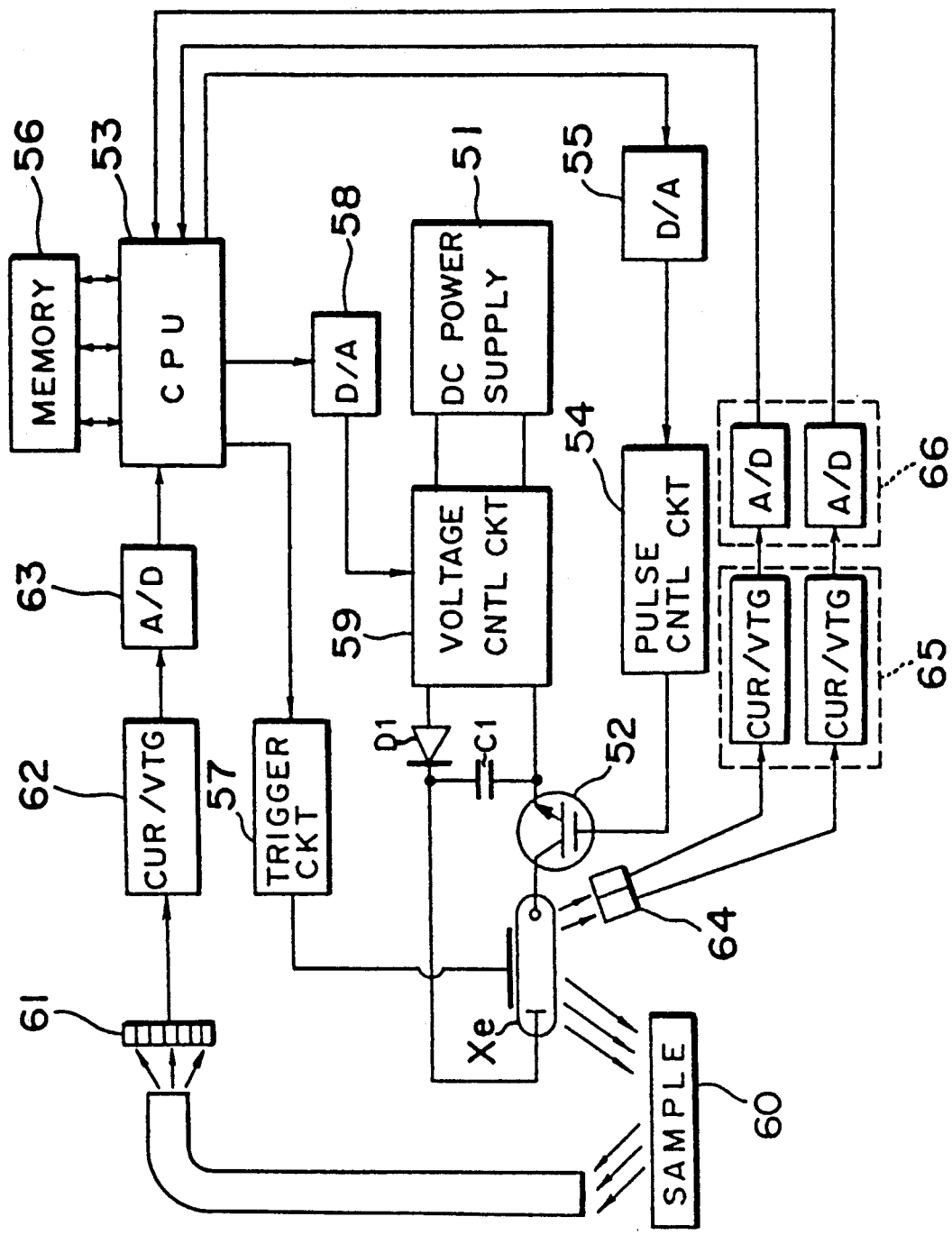
FIG. 13 is a block diagram of a color measuring apparatus in which the flashlight emission apparatus is used.

FIG. 13 is a block diagram showing a color measuring apparatus in which the flashlight emission apparatus is used as a light source or illuminant. Each of spectral light receiving elements 61 of the color measuring apparatus detects a spectral amount of light components of a light reflected by a sample 60 and transmitted through an optical fiber and outputs a current. A current/voltage converter 62 converts the current from the spectral light receiving elements 61 into a voltage. The A/D converter 63 performs the A/D conversion of the signal inputted thereto from the current/voltage converter 62 and outputs the signal of a digital form to the CPU 53.

A DC power supply 51, an IGBT 52, a pulse control circuit 54, and a D/A converter 55 operate similarly to the DC power supply 11, the IGBT 12, the pulse control circuit 14, and the D/A converter 15 shown in FIG. 1, respectively. Photosensors 64, a current/voltage converter 65, and an A/D converter 66 operate similarly to the photosensors 31, a current/voltage converter 32, and an A/D converter 33 shown in FIG. 7, respectively. A voltage control circuit 59 operates similarly to the voltage control circuits 41 shown in FIGS. 8, 9, and 10. A memory 56 stores a table showing the correlation between a color temperature and flashlight emission time as well as measured data.

The color measuring apparatus including the CPU 53 having the above-described construction operates as follows:

An emission control signal is outputted from the CPU 53 to the D/A converter 55. The D/A converter 55 performs the D/A conversion of the emission control signal. Based on the D/A converted emission control signal, the pulse control circuit 54 outputs a gate pulse signal with a predetermined pulse width and a predetermined voltage to the gate of the IGBT 52. In synchronization with the output of the gate pulse signal from the pulse control circuit 54, a trigger circuit 57 is operated by a signal outputted thereto from the CPU 53, which leads to the emission of the flash tube Xe. The level of the gate pulse signal becomes a "L" level when a predetermined time t1 is passed, which causes the IGBT 52 to be turned off. As a result, the flash tube Xe stops the emission immediately.

The light emitted by the flash tube Xe is reflected by the sample 60 and part of the reflected lights enters into the optical fiber. The light which is passed through the optical fiber illuminates the spectral light receiving elements 61. The spectral light receiving elements 61 output photoelectric currents corresponding to an intensity of the incident light at every wavelength bands respectively, then the photoelectric currents are converted into voltages by the current/voltage converter 62. The voltage signal is A/D converted by the A/D converter 63 and then inputted to the CPU 53. Data of the spectral amount of the light reflected by the sample 60 is stored in the memory 56. Thereafter, the CPU 53 calculates a spectral reflectance based on the data of the spectral reflection amount. The spectral reflectance thus obtained is outputted by an output device not shown in FIG. 13.

The photosensors 64 detect amounts of light components of the light emitted by the flash tube Xe in at least two wavelength bands and output signals indicative of the light amounts. The signals from the photosensors 64 are converted into voltages by the current/voltage converter 65, and A/D converted by the A/D converter 66 respectively, then inputted to the CPU 53. Thereafter, the CPU 53 calculates the color temperature of the light emitted by the flash tube Xe based on the input signals indicative of the amounts of light components of the light in the two wavelength bands.

Sensitivity of the color measuring apparatus with the above-described construction can be improved in a wavelength band having a low S/N ratio in the following manner.

Figure 15:
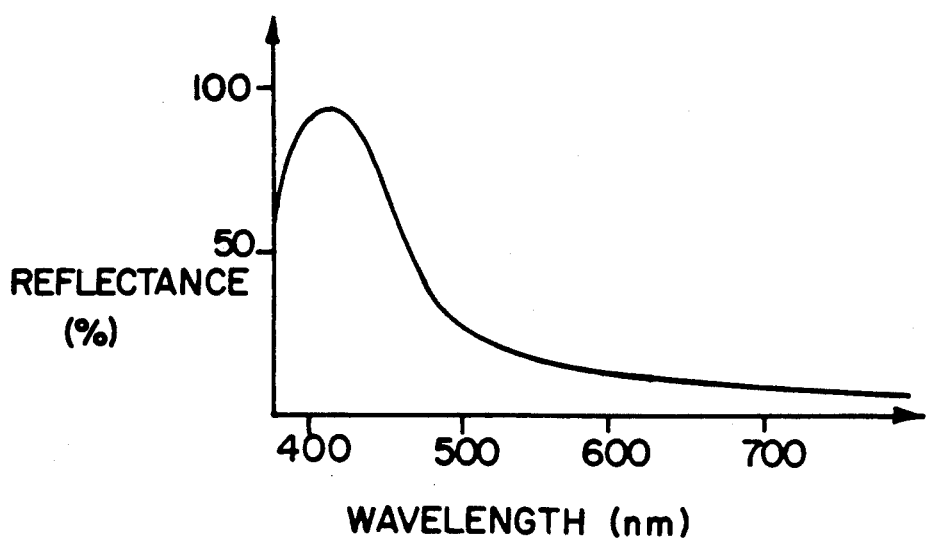
FIG. 15 is a graph showing reflectances measured by the color measuring apparatus whose block diagram is shown in FIG. 13.
Figure 16:
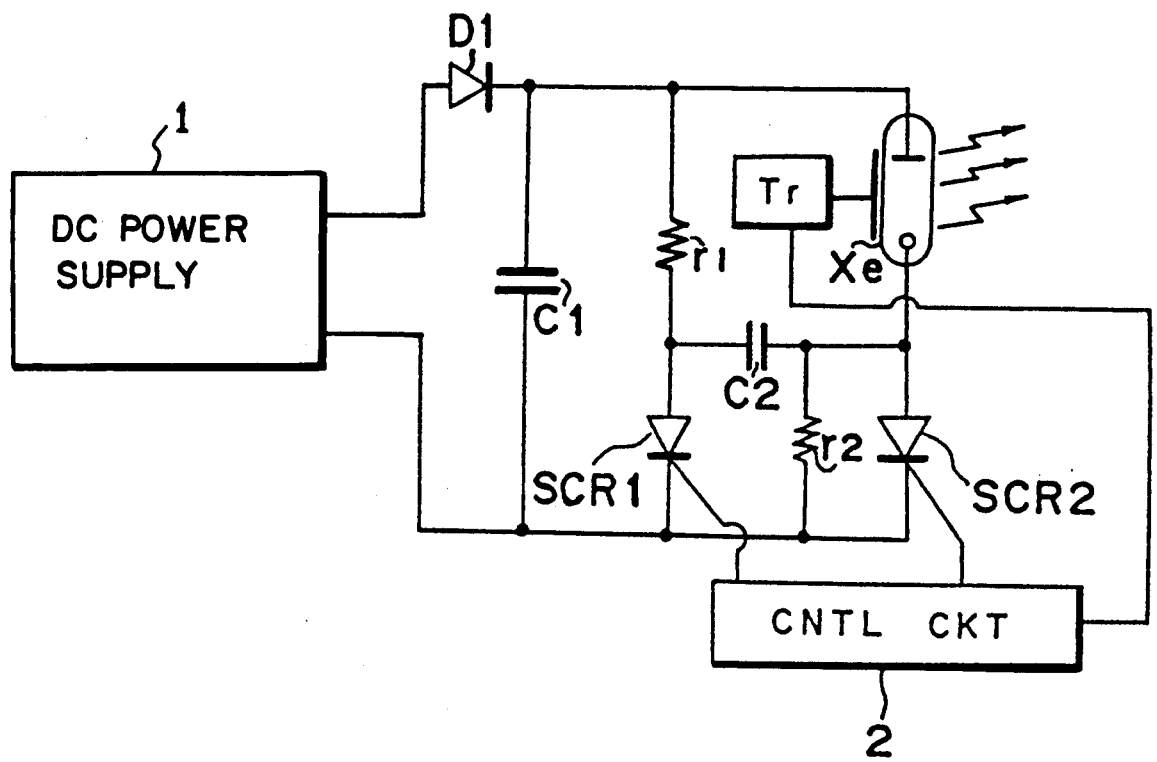
FIG. 16 is a block diagram of a known flashlight emission apparatus.

Suppose that spectral reflectances as shown in FIG. 15 are obtained by a first measurement. As apparent from the graph, short wavelength regions will have preferable S/N ratios, but long wavelength regions will have low reflectances on condition that the intensity at every wavelength of the light source is constant. Therefore, measured values fluctuate among measurements of several times.

Figure 14:
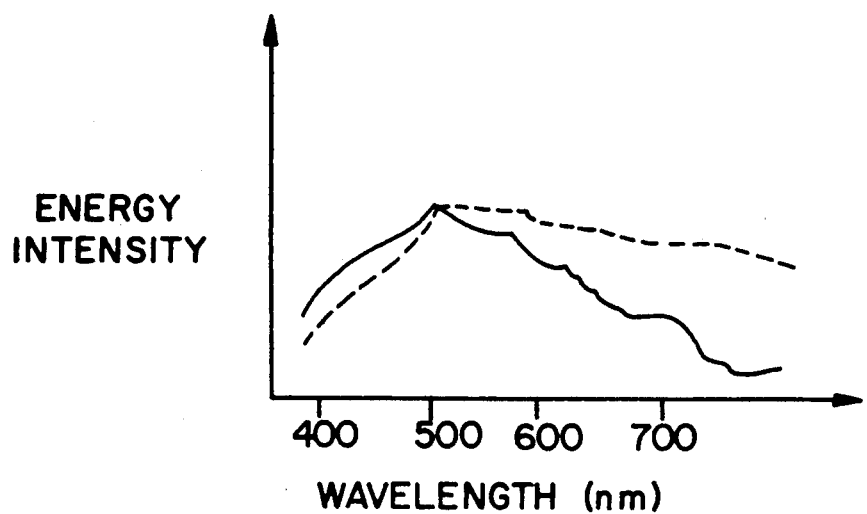
FIG. 14 is a graph showing energy intensities of the flash tube of the color measuring apparatus whose block diagram is shown in FIG. 13.

The S/N ratios in the long wavelength regions can be improved by increasing energy intensities of the light source in the long wavelength regions as shown by a broken line from intensities as a solid line in FIG. 14. Specifically, the S/N ratios in the long wavelength regions can be improved by lowering the color temperature of the light emitted by the flash tube Xe. That is, as understood from FIGS. 4 and 5, the color temperature of the light emitted by the flash tube Xe is lowered by allowing the flash tube Xe to emit a light for a long time or applying a reduced voltage to the flash tube Xe, whereby energy intensities as shown by the broken line in FIG. 14 is obtained. Thus, the S/N ratios in the long wavelength regions can be improved.

If the S/N ratios in the short wavelength regions must be improved by raising the color temperature, it is required to shorten the emission time of the flash tube Xe or to apply an increased voltage to the flash tube Xe.

The method for improving the S/N ratio according to the color measuring apparatus shown in FIG. 13 is described hereinbelow. The CPU 53 detects whether or not the data on the spectral reflectivity obtained as described above includes one wavelength band of a especially lower sensitivity than any other wavelength band. If it is judged that the data on the spectral reflectance include a wavelength band of a low sensitivity, the CPU 53 calculates the condition (namely, the emission time of the flash tube Xe, the voltage of the DC power supply 51 and the gate voltage) for obtaining the color temperature of the flash tube Xe required for improving the S/N ratio of the light emitted therefrom. Based on the calculated condition, as described above, the CPU 53 controls the pulse width and voltage of the gate pulse signal outputted from the pulse control circuit 54 and the voltage of the DC power supply 51 by means of the voltage control circuit 59, whereby the flash tube Xe is capable of emitting lights subsequently having the color temperature calculated by the CPU 53. Accordingly, after the second time measurement, measurements can be carried out with improved S/N ratios.

As described above, according to the color measuring apparatus of this embodiment, the color temperature of the light emitted by the flash tube Xe can be controlled in a wide range with high accuracy. Accordingly, the number of monitoring photosensors can be reduced.

Figure 28A:
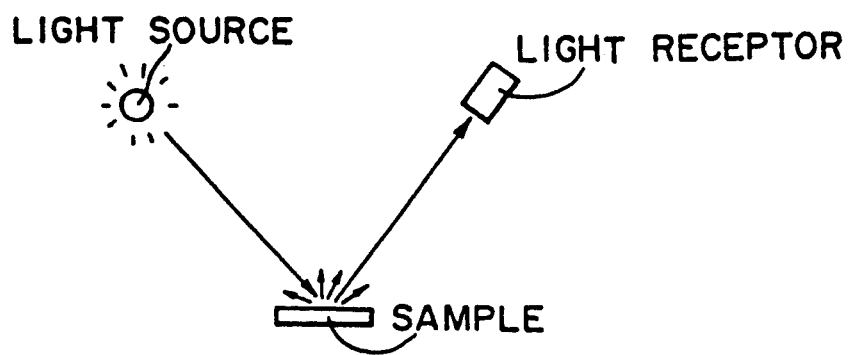
FIGS. 28(a) and (b) are illustrations showing a light reflected by a sample and a light transmitted by a sample, respectively, either of the lights being used for a color measurement.
Figure 28B:
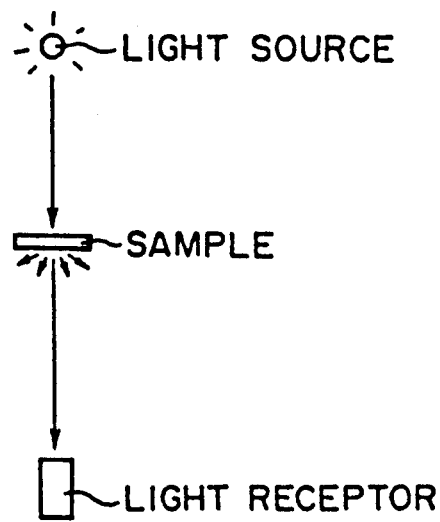

The color measuring apparatus measures the reflectances by using light components reflected from the sample 60 as shown in FIG. 28(a), but it may perform its function by measuring a transmittance by using lights which have been transmitted by the sample 60 as shown in FIG. 28(b).

According to the flashlight emission apparatus, the color temperature of the light emitted by the flash tube is controlled by changing the pulse width of the gate pulse signal. Accordingly, the turn-off time of the switching element can be shortened, so that the overemission amount, that is, amount of the flashlight emitted by the flash tube Xe during the turn-off operation is small and gets constant. Thus, according to the present invention, the color temperature of the light emitted by the flash tube can be controlled at a constant value.

The emission amount calculating means provided in the flashlight emission apparatus in accordance with the above embodiment calculates the emission amounts detected by the photosensors by means of the emission amount accumulating means and compares the accumulated emission amount with a specified emission amount. Based on the result thus compared, the number of times of emissions of the flash tube is controlled by the control means. Accordingly, the light amount per emission can be made to be constant, which allows an effective control of the total amount of the light emitted by the light source.

According to the flashlight emission apparatus of the present invention of the above embodiment capable of controlling the number of times of emissions of the flash tube Xe, the color temperature calculating means calculates the color temperature difference between a color temperature of the light emitted by the flash tube and a specified color temperature based on the emission amounts of the flashlight in at least two wavelength regions detected by the photosensors. Further, the pulse width of the gate pulse signal to be subsequently outputted is controlled by means of the correlation table stored in the memory according to the calculated color temperature difference. Therefore, the color temperature of the light emitted by the flash tube can be controlled to have the specified color temperature. Further, since the flashlight emission apparatus is capable of carrying out a stable emission by the use of the insulated-gate bipolar transistor (IGBT), the number of monitoring parts can be reduced. Accordingly, the flashlight emission apparatus can be manufactured at a low cost.

Since the charge voltage control means of the flashlight emission apparatus in accordance with the above embodiment can change the voltage to be applied to the main capacitor, the color temperature of the light emitted by the flash tube Xe can be set to a specified color temperature by controlling either the voltage to be applied to the main capacitor or the pulse width of the gate pulse signal, or both. Accordingly, the color temperature can be controlled in a broad range with high accuracy.

Since the gate voltage control means of the flashlight emission apparatus in accordance with the present invention changes the voltage of the gate pulse signal, controlling of the color temperature of the light emitted by the flash tube Xe is effected by controlling the voltage of the gate pulse signal, the pulse width thereof and/or the charge voltage of the main capacitor. Accordingly, the color temperature can be controlled in a wider range with high accuracy.

The color measuring apparatus of the above embodiment comprising the flashlight emission apparatus and the spectral light receiving elements is capable of detecting the spectral light amount of each light which has been reflected or transmitted by a sample, according to the switching operation of the insulated-gate bipolar transistor (IGBT). According to this construction, when it is judged by the CPU that the color measurement is carried out with respect to a sample having a wavelength band in which the spectral reflectance or the spectral transmittance is low, at least one of the charge voltage of the main capacitor, the pulse width of the gate pulse signal and the pulse voltage thereof is controlled based on the output from the spectral light receiving elements, whereby the amount of the light emitted by flashlight emission apparatus can be increased in a wavelength band of a low reflectivity or a low transmittance. Therefore, according to the present invention, the S/N ratio in the wavelength region of a low reflectivity or a low transmittance can be improved. Further, since the color measuring apparatus is capable of performing a stable emission by means of the insulated-gate bipolar transistor (IGBT), the number of monitoring parts can be reduced. Therefore, the color measuring apparatus can be manufactured at a low cost.

Figure 18:
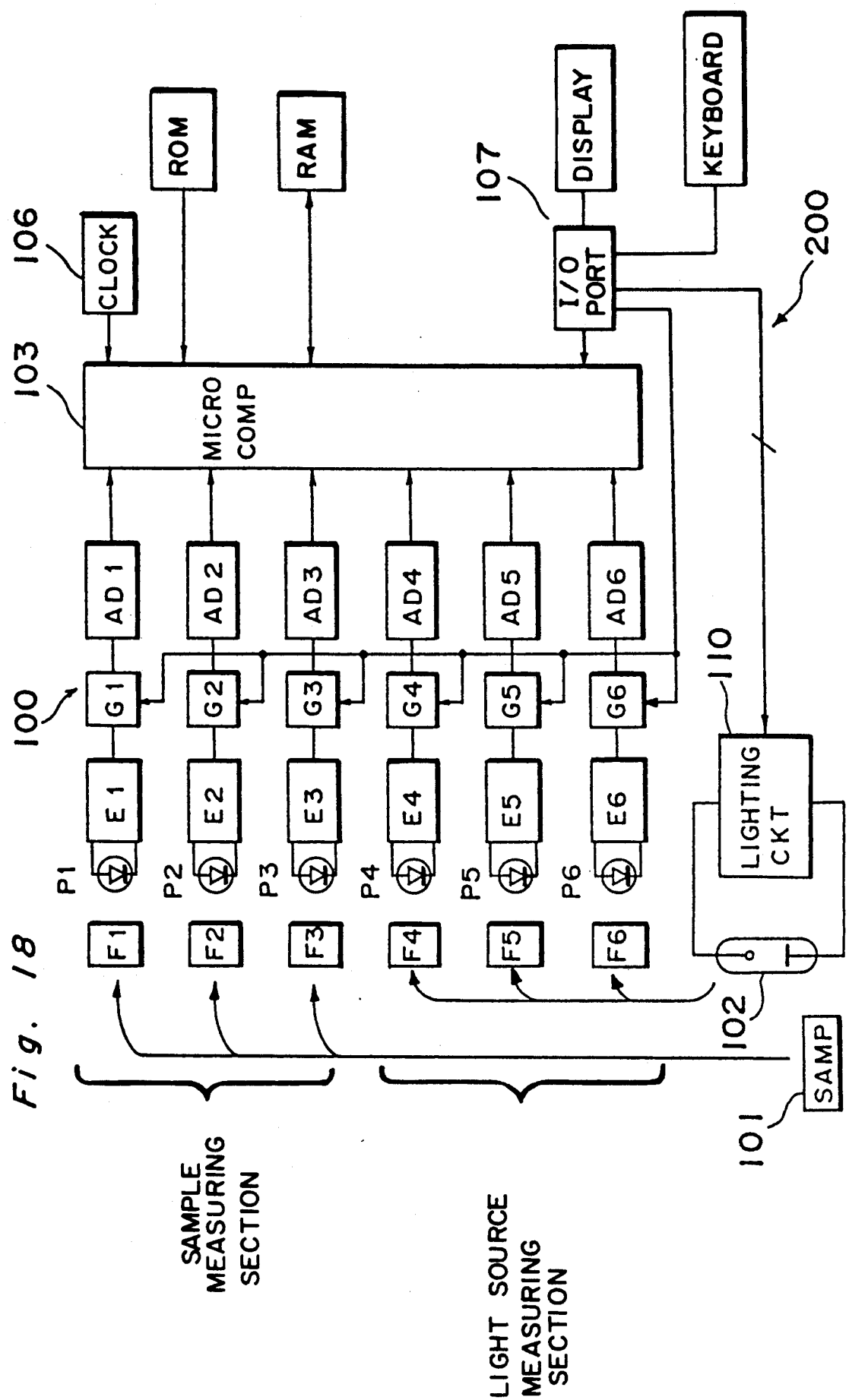
FIG. 18 is a block diagram showing an entire construction of an embodiment of a color measuring apparatus of the present invention.

FIG. 18 is a block diagram showing the entire construction of a color measuring apparatus of a further embodiment of the present invention. As shown in FIG. 18, the color measuring apparatus comprises a photoelectric conversion section 100 and a data processing section 200. The photoelectric conversion section 100 includes a light source 102 and six photodiodes P1 through P6 for converting light components of a light into an electric current. The photodiodes P1 through P3 are used to measure reflected light from a sample 101 with illuminating by the light source 102, and the photodiodes P4 through P6 are used to measure (monitor) lights emitted by the light source 102.

Combinations of the photodiodes P1 through P3 and filters F1 through F3 arranged before the photodiodes respectively are constructed as light receiving systems in such a manner as to have constitute spectral sensitivities approximate to a primary colors isochromatic function $x_2(\gamma)$, $y(\gamma)$, $z(y)$ which conforms with CIE standards. As another light receiving systems, combinations of photodiodes P4 through P6 and filters F4 through F6 arranged before the photodiodes are similarly constructed.

Lights coming from the sample 101 and the light source 102 pass through the filters F1 through F6 and detected by the photodiodes P1 through P6, respectively. Electric currents outputted from the photodiodes P1 through P6 are converted into electric voltage signals by photoelectric converter circuits E1 through E6, and the electric signals corresponding to light intensities are transferred to A/D converter circuits AD1 through AD6 through gates G1 through G6, respectively. The A/D converter circuits convert the electric signals into digital signal corresponding to the light intensities. The digital signals are inputted to and stored in a microcomputer 103 which controls the data processing section 200.

Supposing that the outputs from the A/D converter circuits AD1 through AD6 have values XS, YS, ZS, XR, YR, and ZR respectively, the microcomputer 103 calculates XS/XR, YS/YR, and ZS/ZR, thus cancelling a fluctuation of the light amounts of the light source 102.

The data processing section 200 comprises the microcomputer 103 which controls and calculates, a read only memory (ROM) 104 for storing programs such as ones for the system control and color space transformation, a random access memory (RAM) 105 as memory means for storing color information or a table indicating the correlation between the flashlight emission time and the color temperature of a xenon tube, a clock generator 106, an I/O port 107, a display section 108 such as a liquid crystal display device and a printer for displaying results obtained by a measurement, and a keyboard 109 for performing the operation.

A xenon flash lamp is used as the light source 102 and the color measuring apparatus is provided with a lighting circuit 110 for making the xenon flash lamp emit or stop emitting light.

Next, the color temperature of the light emitted by the light source 102, namely, the xenon flash tube (hereinafter referred to as xenon tube) is described hereinbelow. The color temperature of light emitted by the xenon tube depends on the electric current which flows through the xenon tube when the xenon tube emits the flashlight, as described before.

Figure 21A:
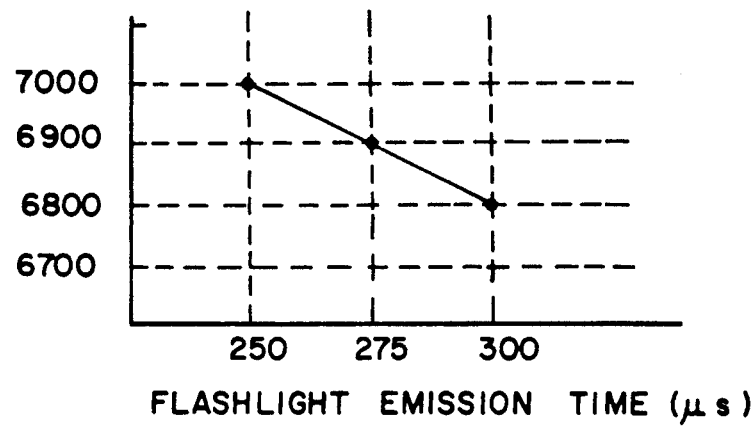
FIG. 21(a) is a graph showing the relationship between the color temperature and flashlight emission time of a xenon tube when the tube is cooled.

As apparent from FIGS. 21(a) and (b), in heated state the color temperature drops than that in cooled state due to the rise of the temperature of the light source 102. It can be avoided by appropriately adjusting the flashlight emission time so that the color temperature rises, whereby a measurement can be accomplished at a constant color temperature.

Figure 19:
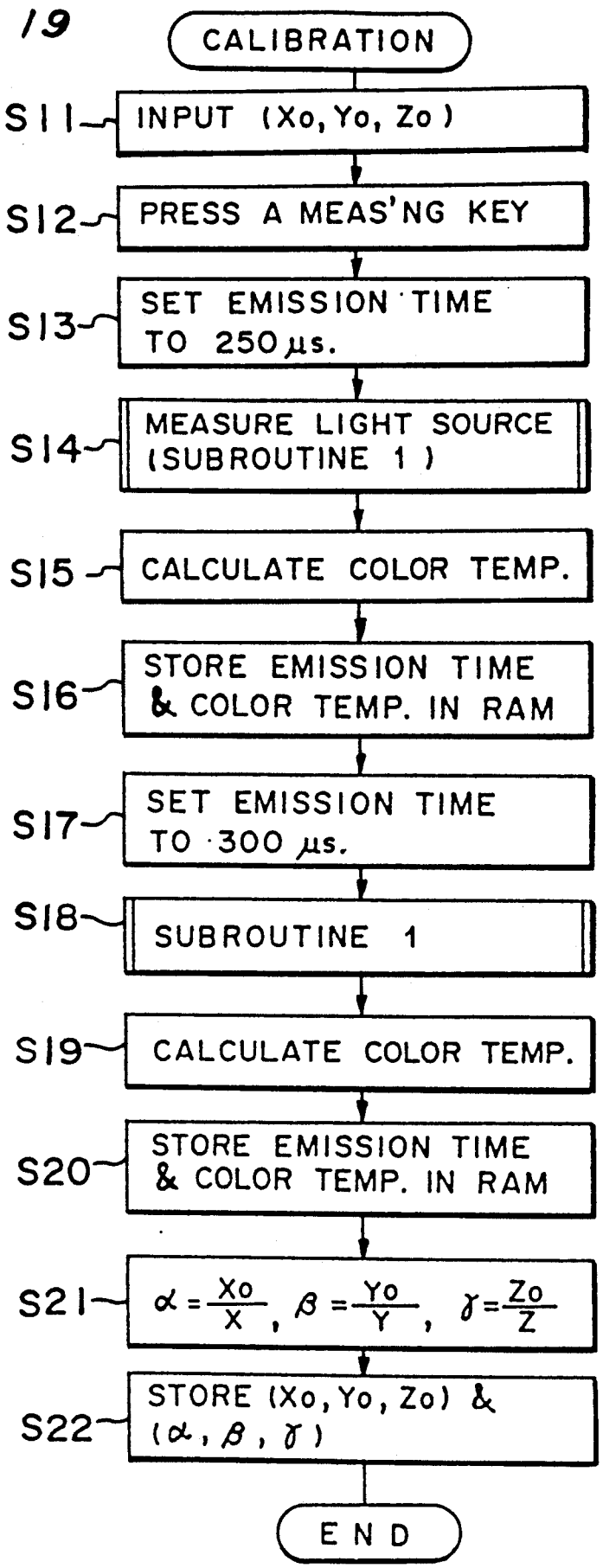
FIG. 19 is a flowchart showing a calibration operation carried out by the color measuring apparatus of FIG. 18.

The measuring operation is described referring to the flowchart shown in FIG. 19.

It is necessary to carry out a calibration in using the color measuring apparatus. That is, it is necessary to obtain data on the correlation between the emission time and the color temperature of the flashlight emitted by the light source 102 and determine calibration constants of the color measuring apparatus by using a standard calibration sample.

Figure 20:
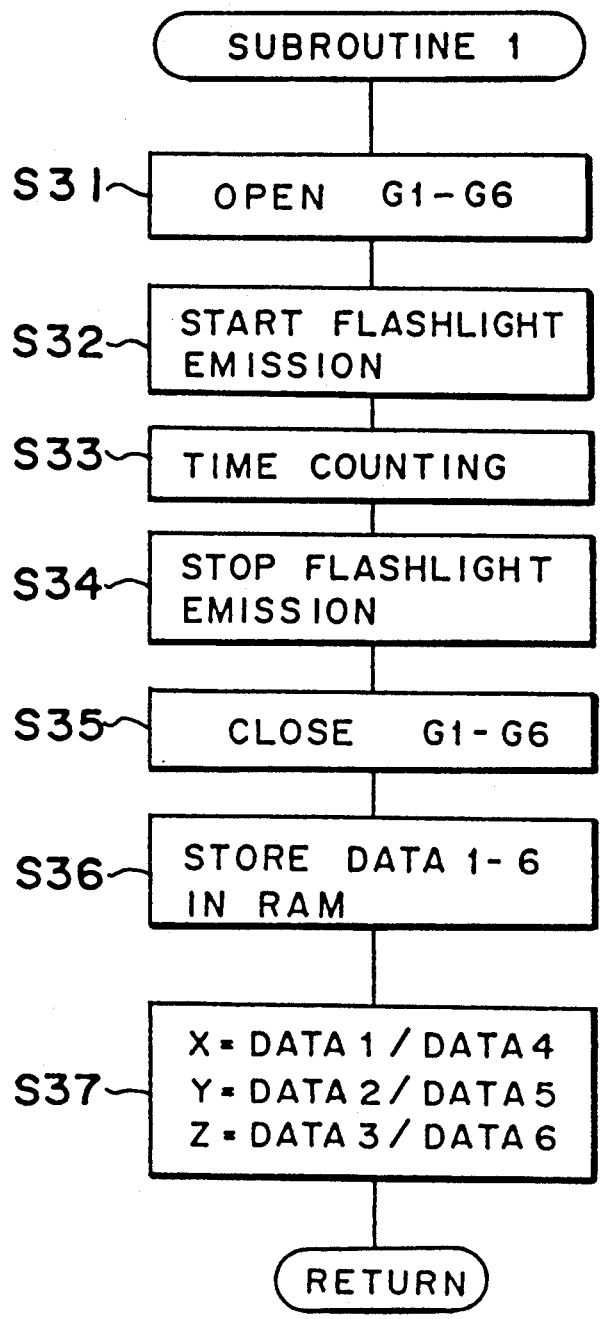
FIG. 20 is a flowchart of a subroutine carried out during the calibration operation.

First, a calibration key on the keyboard 109 is pressed to allow the program to go into the calibration mode. At step S11, tristimulus values Xo, Yo, and Zo of a calibration standard sample are inputted with numerical keys on the keyboard 109. At step S12, a measuring key of the keyboard 109 is pressed. At step S13, the flashlight emission time is set to 250 μs. At step S14, a subroutine 1 shown in FIG. 20 is called to measure the light coming from the light source 102.

In the subroutine 1, the gates G1 through G6 are opened at step S31. At step S32, the xenon tube start to emit a flashlight. At step S33, a specified time is counted during which the xenon tube keeps emitting flashlight. At step S34, the xenon tube is stopped from emitting the flashlight since the specified time has passed. At step S35, the gates G1 through G6 are closed. At step S36, the microcomputer 103 receives the digital values DATA 1 through DATA 6 outputted from the A/D converter circuits AD1 through AD6 and stores them in the respective storing addresses of the RAM 105. At step S37, the following calculations are performed.

$$X = DATA1/DATA4$$

$$Y = DATA2/DATA5$$

$$Z = DATA3/DATA6$$

Then, the program goes back to the main routine and proceeds to step S15 of FIG. 19 at which the color temperature of the light source 102 is calculated by using the DATA 4 through DATA 6. At step S16, DATA 10 indicating the flashlight emission time of 250 μs and DATA 11 indicating the calculated color temperature value are stored in the corresponding addresses of the memory 105. At step S17, the flashlight emission time is set to 300 μs and after a specified time elapses, the subroutine 1 is called again at step S18. At step S19, the color temperature of the light source 102 is calculated by using current data DATA 4 through DATA 6 for the tristimulus of the flashlight emitted by the light source 102. At step S20, DATA 12 representing flashlight emission time of 300 μs and DATA 13 representing the current color temperature value obtained at step S19 are stored in the corresponding addresses of the memory 105. At step S21, calibration constants $\alpha$, $\beta$ and $\gamma$ are found by performing the following calculations:

$$\alpha = Xo/X, \beta = Yo/Y, \gamma = Zo/Z$$

The above X, Y, and Z are the data calculated at step S37 of the subroutine carried out at step S18 of FIG. 19. In the above equations, Xo, Yo, and Zo are the tristimulus values of the calibration standard sample inputted at step S11. That is, the calibration constants are determined by setting the flashlight emission time of 300 μs as the standard flashlight emission condition. At step S22, the tristimulus values Xo, Yo, and Zo and the calibration constants $\alpha$, $\beta$, and $\gamma$ are stored in the memory 105. Thus, the calibration is completed.

In the above description, the correlation between the flashlight emission time and the color temperature of the light emitted by the xenon tube is found at only two points (250 μs and 300 μs), but a color measurement can be carried out with a higher accuracy by finding the correlation between the flashlight emission time and the color temperature every 1 μs, for example, 250 μs, 251 μs, ... 300 μs. The correlation between the flashlight emission time and the color temperature may be also obtained every 10 μs and approximate values obtained through a linear interpolation or a curve interpolation may be used for the remaining points.

The following describes the operation of measuring the tristimulus values XM, YM, and ZM of a sample 101 by the use of the color measuring apparatus.

Figure 21B:
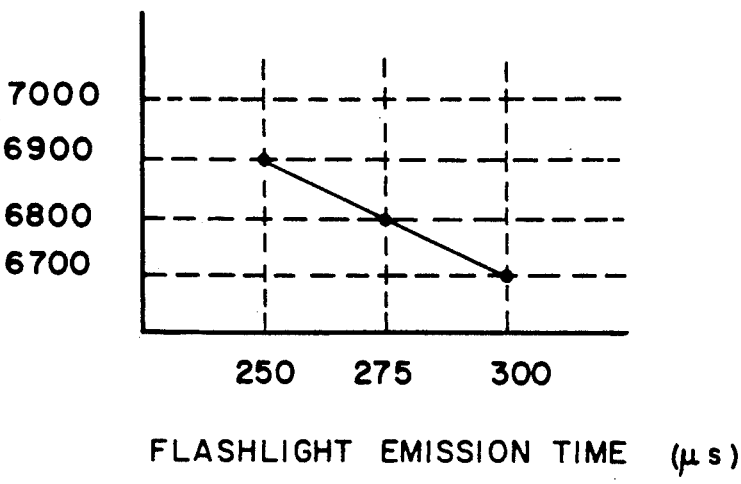
FIG. 21(b) is a graph showing the relationship between the color temperature of the emission and the flashlight emission time of the xenon tube when the tube is heated.

FIGS. 21(a) and 21(b) also show the relationship between the flashlight emission time and the color temperature of the xenon tube in the state in which the xenon tube is cooled and heated, respectively. Generally, calibration constants $\alpha$, $\beta$, $\gamma$ are found when the xenon tube is cooled. That is, according to the embodiment, the calibration constants $\alpha$, $\beta$, and $\gamma$ according to the embodiment are values obtained when the flashlight emission time of the xenon tube is 300 μs and the color temperature is 6800 K. The graph of FIG. 21(b) indicates that in order to keep the color temperature at 6800 K, the flashlight emission time is changed to, for example, 275 μs when the xenon tube is heated.

Figure 22:
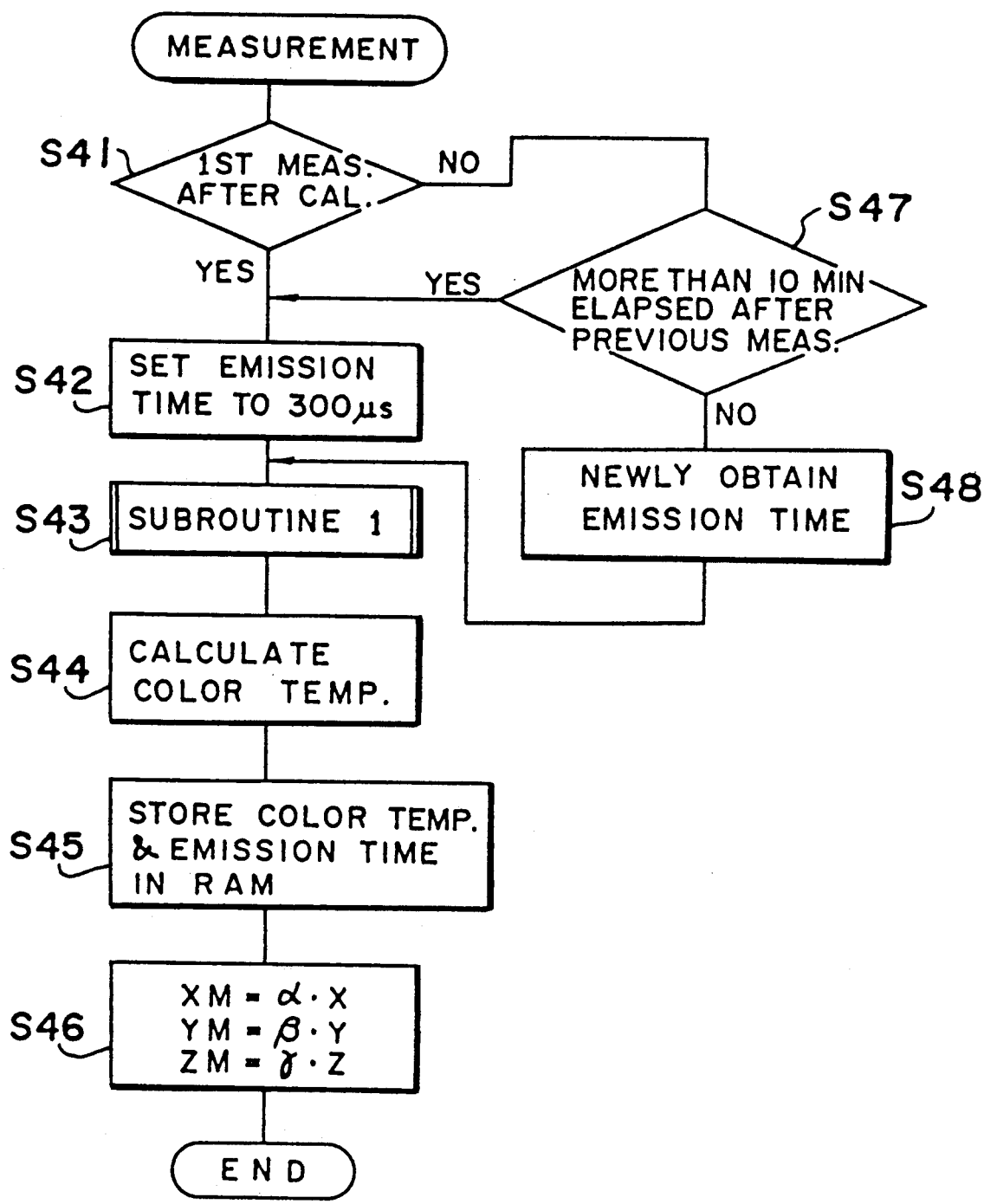
FIG. 22 is a flowchart showing the operation to be performed in a measurement.

A method for measuring the tristimulus values XM, YM, and ZM is described with reference to a flowchart shown in FIG. 22 hereinbelow. It is detected at step S41 whether or not the measurement is performed for the first time after the calibration is completed. If yes, the program goes to step S42. If no, the program goes to step S47. At step S42, the flashlight emission time of the xenon tube is set to 300 μs. At step S43, the subroutine 1 is called to find the data DATA 4 through DATA 6 stored in the memory 105 necessary for calculating the values of X, Y, and Z and the color temperature of the light emitted by the light source 102, or the xenon tube. At step S44, the color temperature of the light emitted from the light source 102 is calculated based on the data DATA 4 through DATA 6. At step S45, DATA 100 representing the color temperature obtained at step S44 and DATA 101 representing the flashlight emission time are stored in the memory 105. At step S46, tristimulus values XM, YM, and ZM of the sample 101 are calculated by the following equations:

$$XM = \alpha \cdot X$$

$$YM = \beta \cdot Y$$

$$ZM = \gamma \cdot Z$$

It is discriminated at step S47 whether or not more than 10 minutes elapsed after the previous measurement is carried out. The measurement routine has this step S47 for the following reason. Prior to the current measurement, one or more measurements were already carried out after the calibration was completed. Therefore, the color temperature may have changed because of the temperature rise of the xenon tube. If it is decided that more than 10 minutes has elapsed, the program goes to step S42. If no, the program goes to step S48. At step S48, according to the DATA 100, 101 and the data on the correlation between the color temperatures and the flashlight emission times which are found when the calibration was carried out, a next emission time is found so that the color temperature becomes the same as the DATA 13, namely, the color temperature measured when the emission time is 300 μs under the condition in which the xenon tube is cooled. The next flashlight emission time is found by the following equation, for example, based on the correlation table.

$$\text{Emission time} = DATA101 + (DATA13 - DATA100) \times (DATA10 - DATA12)/(DATA11 - DATA13)$$

where DATA 10–13 are values obtained when the calibration was carried out. Specifically, the values are: DATA 10=250 μs, DATA 11=7000 K, DATA 12=300 μs, and DATA 13=6800 K. The DATA 100 and 101 represent the color temperature and emission time of the light source 102 obtained at the previous measurement, respectively. The above calculation is performed by the microcomputer 103.

In this equation the meaning of each term is as follows:

DATA 10: Flashlight emission time of 250 μs used in the calibration;
DATA 12: Flashlight emission time of 300 μs used in the calibration;
DATA 11: Color temperature at the emission time of 250 μs; and
DATA 13: Color temperature at the emission time of 300 μs.

The multiplicand (DATA 10-DATA 12)/(DATA 11-DATA 13) in the above equation is the rate of change of the flashlight emission time per unit color temperature, for example, 1 K. The multiplicator (DATA 13-DATA 100) is the difference between the color temperature measured at the previous time and the target color temperature. This value is the temperature difference to be corrected. The flashlight emission time to be changed from the previous flashlight emission time is represented by the product of the multiplicator (DATA 13-DATA 100) by the multiplicand (DATA 10-DATA 12)/(DATA 11-DATA 13). Accordingly, the addition of this value to the DATA 101 indicating the previous flashlight emission time provides a next current flashlight emission time. The temperature of the xenon tube gradually returns to the initial temperature with the lapse of time after the completion of the flashlight emission. In this embodiment, a flashlight emission time for the current measurement is obtained from the above equation without considering the lapse of time if the current measurement is carried out within ten minutes from the previous one. Therefore, if a time interval between the previous measurement and the current measurement happens to be longer than the specified time interval during repeated measurements, the current flashlight emission time is excessively compensated, that is, the color temperature gets much higher than it should be. In this case, however, the flashlight emission time for the next measurement is set to be longer. Therefore, the color temperature converges toward the targeted value of 6800 K.

As described above, the first measurement after the calibration is carried out with the emission time being 300 μs which was used for obtaining the calibration constants α, β, and γ. From the second measurement, the flashlight emission time for each measurement is calculated in such a manner as to obtain the same color temperature as DATA 13, based on the color temperature of the xenon tube and flashlight emission time of the previous measurement and the correlation table obtained during the calibration. If the current measurement is carried out more than 10 minutes after the previous measurement is effected, the DATA 12 indicating 300 μs is adopted as the flashlight emission time.

Because the temperature of the xenon tube gradually falls with the lapse of time, it is necessary to consider the influence which is give to the color temperature by the lapse of time gradually. To this end, for example, the following method can be adopted to modify the flashlight emission time gradually. The product of the difference between the flashlight emission time in the current measurement and the standard flashlight emission time 300 μs by a coefficient is set as a correction time. The coefficient linearly decreases from 1 to 0 corresponding to the time lapse after the previous measurement immediately to 10 minutes. The correction time thus obtained is subtracted from or added to the standard flashlight emission time of 300 μs.

Figure 23:
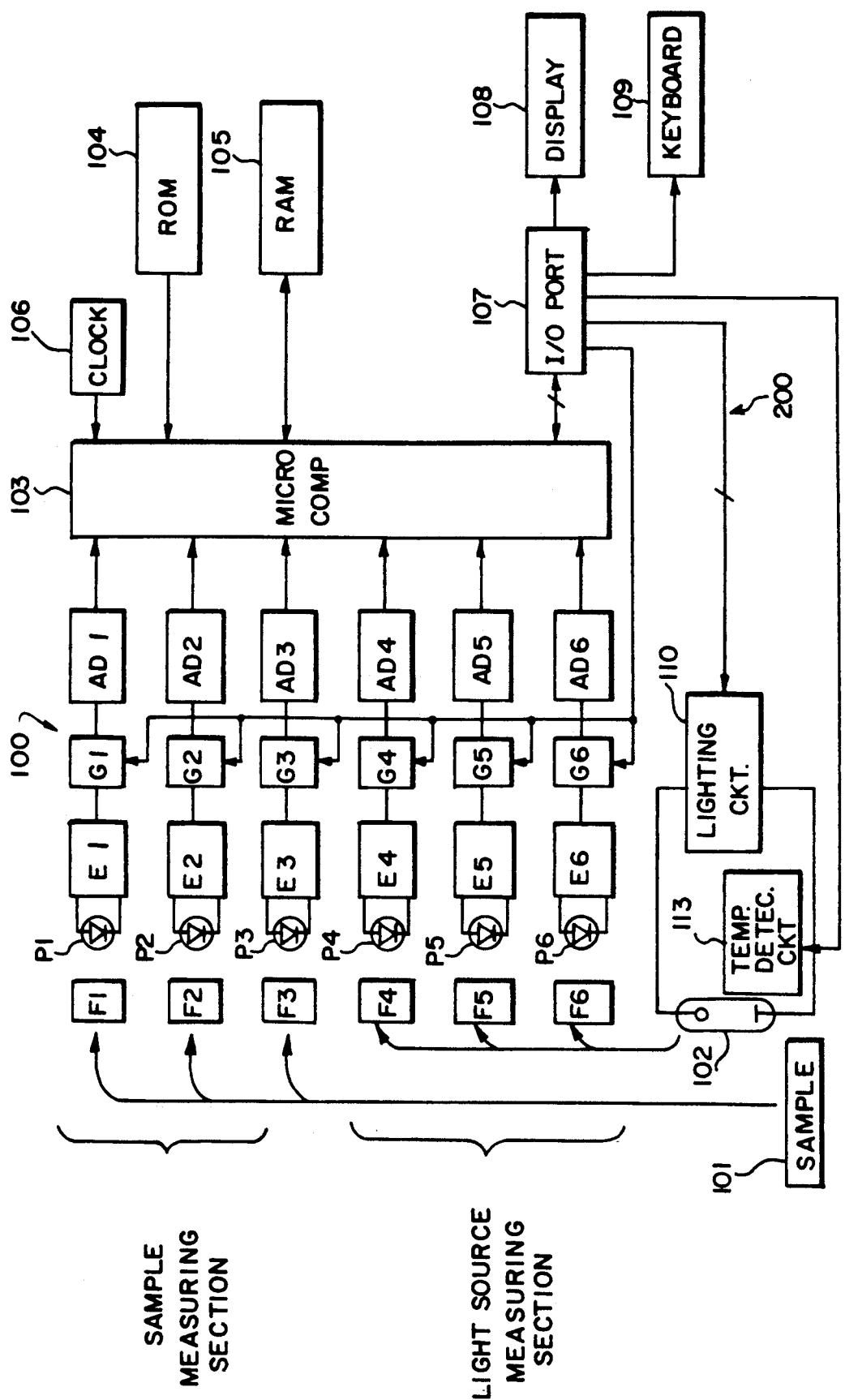
FIG. 23 is a block diagram of another embodiment of a color measuring apparatus the present invention.
Figure 24:
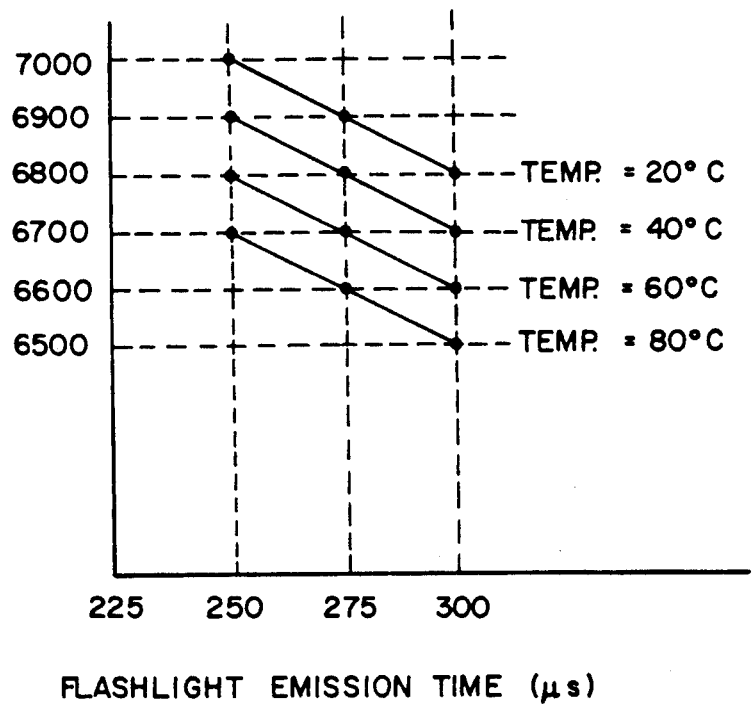
FIG. 24 is a graph showing the relationship between the color temperature and flashlight emission time of a xenon tube with the temperature of the xenon tube being a parameter.

In order to obtain the target color temperature with higher accuracy, the color measuring apparatus is provided with a temperature detecting circuit 113 for measuring the temperature of the light source 102 as shown in FIG. 23. And the memory 105 stores a table as shown in FIG. 24 indicating the correlation between the color temperature and the flashlight emission time of the xenon tube which is obtained when the calibration is performed or before the color measuring apparatus is shipped from the factory. In this embodiment, the portions corresponding to those shown in FIG. 18 are denoted by the same reference numerals as those shown in FIG. 18 and the description thereof are omitted.

In the above-described embodiment, the color measurement is described with reference to a color measuring apparatus of a type that the tristimulus values are directly read, but a color measuring apparatus of spectrum analysis system may be also used.

Figure 25:
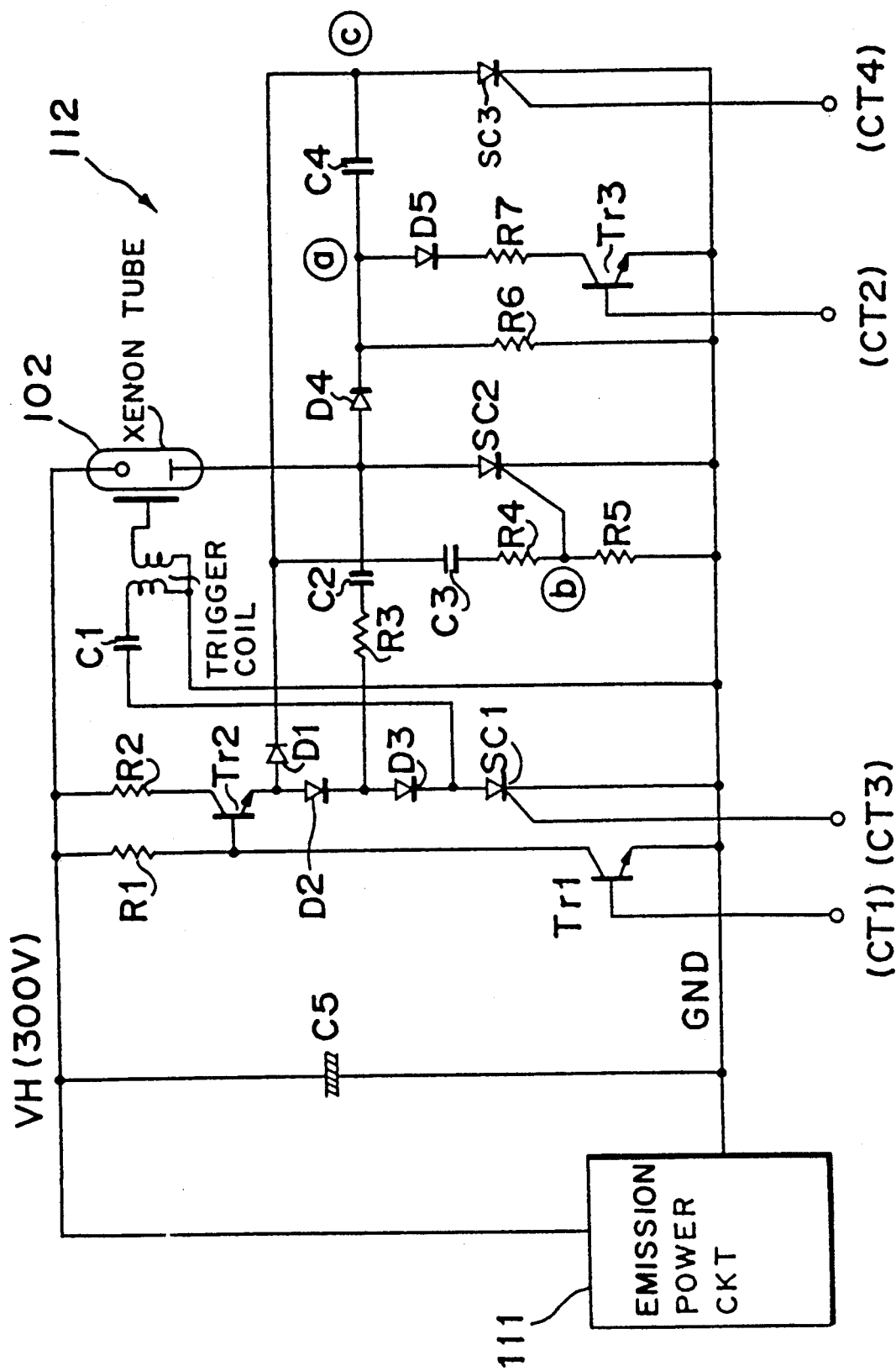
FIG. 25 is a circuit diagram of a lighting circuit of the embodiment.
Figure 26:
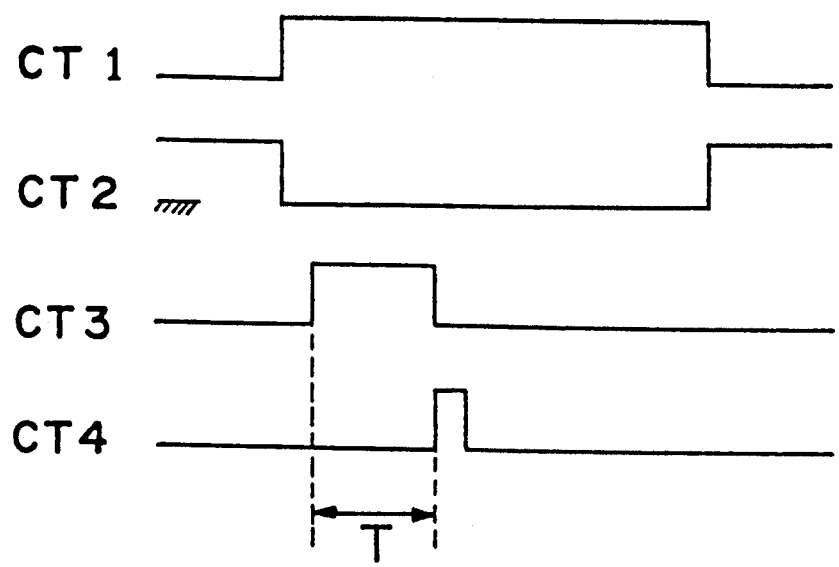
FIG. 26 is a timing chart of signals in the lighting circuit.
Figure 27:
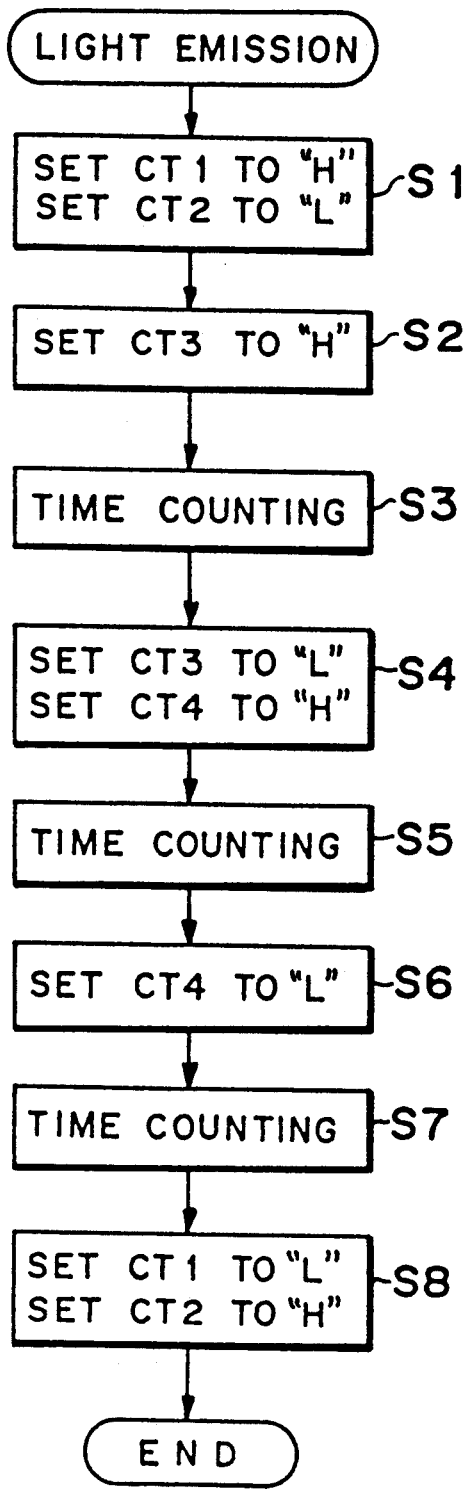
FIG. 27 is a flowchart showing the operation of the lighting circuit.

Finally, the construction and operation of the lighting circuit 110 are described hereinbelow. FIG. 25 shows an example of the lighting circuit 110. FIG. 26 is a timing chart of a signal outputted from the microcomputer 103 for operating the lighting circuit 110. FIG. 27 is a flowchart showing the operation.

In FIG. 25, reference symbols CT1 through CT4 denote control signals controlled by the microcomputer 103 and the I/O port 107. The lighting circuit 110 comprises an emission power circuit 111 for generating the voltage of 300 V necessary for allowing the light source 102 to emit a light and an emission control circuit 112 for controlling light emissions of the xenon tube. In the standby state of the emission control circuit 112, the levels of the control signals CT1, CT3, and CT4 are low "L" and the level of the control signal CT2 is high "H". Since the level of the control signal CT1 is "L", a transistor Tr1 is OFF and a transistor Tr2 is ON. At this time, electric current flows in the order of a capacitor C5, a resistor R2, the transistor Tr2, a diode D1, a capacitor C4, a diode D5, a resistor R7, a transistor Tr3, and a ground GND. Thus the capacitor C4 is charged. Capacitors C1, C2, and C3 are also charged.

The light emission and its stop of the light source 102 are described in accordance with the flowchart shown in FIG. 27.

When an emission of the xenon tube is requested, the level of the control signal CT1 is set to "H" and the level of the control signal CT2 is set to "L" at step S1. Consequently, the transistors Tr2 and Tr3 are turned off and electric current does not flow to the capacitors C1–C4.

Thereafter, the program goes to step S2 at which the level of the control signal T3 is set to "H", whereby a thyristor SC1 is turned on and the capacitor C1 is rapidly discharged. As a result, a voltage of minus several kilovolts is generated on the secondary side of a trigger coil, and the voltage is applied to a trigger line of the xenon tube, which causes the xenon tube to start a flashlight emission. At this time, the voltage at the point ⓐ indicated in FIG. 25 is raised to a voltage of VH of the emission power circuit 111. The differentiation operation through the capacitors C4 and C3 raises a voltage at the point ⓑ, then a thyristor SC2 is turned on. Thus, a great amount of electric current circulates via the capacitor C5, the xenon tube, the thyristor SC2, and the ground GND in that order, and the xenon tube starts emitting a flashlight. Thereafter, the program goes to step S3 at which the program waits for the termination of a specified flashlight emission time. When the waiting for the specified time terminates, the program goes to step S4 at which the level of the control signal CT3 is set to "L" and the level of the control signal CT4 is set to "H". Consequently, the thyristor SC3 is turned on and a voltage at the point ⓒ rapidly falls from VH to the voltage of the GND. The voltage at the point ⓐ turned to a minus level temporally due to the differentiation operation of the capacitor C4. And the electric current which was circulating via the capacitor C5, the xenon tube, the thyristor SC2, and the ground GND in that order until then starts to circulate via the capacitor C5, the xenon tube, the diode D4, the capacitor C4, the thyristor SC3, and the GND in that order. The electric current continues flowing until the capacitor C4 cannot be charged any more. When the electric current does not flow any more to the capacitor C4, no electric current flows through the xenon tube because the thyristor SC2 has already been turned off. As a result, the xenon tube stops the emission.

While the electric current circulates via the capacitor C5, the xenon tube, the diode D4, the capacitor C4, the thyristor SC3, and the ground GND, the program goes to step S5, and waits for several hundreds of microseconds, then, the program goes to step S6 at which the control signal CT4 is set to "L". At this time, the xenon tube has already stopped emitting a flashlight. Then, the program goes to step S7 at which the program waits approximately 10 msec. This time duration is necessary for the internal impedance of the xenon tube to become sufficiently large. If the program goes to step S8 without this waiting at step S7, there is a possibility that the xenon tube undesirably emits a flashlight because the internal impedance of the xenon tube is small. Then, the program goes to step S8 at which the level of the control signal CT1 is set to "L" and the level of the control signal CT2 is set to "H", and now, the xenon tube is ready for an emitting.

As apparent from the above-described flow, the emission time of the light source can be adjusted by the microcomputer 103 through the adjustment of waiting time at step S3 at which the program waits for the termination of a predetermined flashlight emission time.

Of course, it is desirable in the lighting circuit 110 to use insulated-gate bipolar transistor to replace the thyristor SC2.

As described above, a color temperature of light emitted by a xenon tube also changes according to a temperature of the xenon tube, and as such, the color temperature can be controlled by changing a flashlight emission time of the xenon tube. The present invention was made utilizing this. Accordingly, a color temperature of light emitted by the xenon tube is detected and flashlight emission time is controlled so that the color temperature becomes a target value. Accordingly, if measurements are repeated in a short time, a drift does not occur in the measured color temperatures, i.e., a colorimetry can be accomplished with high accuracy.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. Color measuring apparatus for measuring color of a sample comprising:
   a light source positioned so as to illuminate the sample;
   means for detecting color temperature of light coming from the light source without passing through the sample and without being reflected by the sample;
   means for storing a relationship between a plurality of color temperatures and a plurality of emission time periods of the light source;
   means for comparing the color temperature detected by the detecting means with a predetermined color temperature and for providing a comparison result representative thereof;
   means for determining a certain time period on the basis of both the relationship stored in the storing means and the comparison result of the comparing means;
   means for energizing the light source during the time period determined by the determining means;
   means for detecting light from the sample illuminated by the light source; and
   means for measuring a color of the sample in accordance with the light detected by the detecting means.

2. Color measuring apparatus for measuring a color of a sample comprising:
   a light source positioned so as to illuminate the sample;
   first detecting means for detecting the temperature of the light source;
   means for storing a relationship between a plurality of temperatures and a plurality of emission time periods of the light source;

means for determining a certain time period on the basis of the relationship stored in the storing means and the temperature detected by the first detecting means;

means for energizing the light source during the time period determined by the determining means;

second detecting means for detecting light from the sample illuminated by the light source; and means for measuring a color of the sample in accordance with the light detected by the second detecting means.

3. Lighting apparatus comprising:

a flash tube;

a capacitor for storing electric charge to be supplied to the flash tube so that the flash tube emits light;

power supply circuit for charging the capacitor;

means for storing a relationship between a plurality of emission time periods of the flash tube and a plurality of color temperatures of the flash tube;

means for designating a color temperature;

means for calculating a time period on the basis of the designated color temperature and of the relationship stored in the storing means; and means for controlling a time period of a light emission of the flash tube in accordance with the time period calculated by the calculating means.

4. The lighting apparatus of claim 3, wherein said controlling means include:

means for triggering the emission of the flash tube; and means for interrupting the emission of the flash tube by stopping an electric charge current to the flash tube when the time period calculated by the calculating means elapses from the timing of the triggering of the triggering means.

5. The lighting apparatus of claim 3, further comprising means for controlling total quantity of successive light emissions of the flash tube by controlling the number of emission times of the flash tube.

6. The lighting apparatus of claim 5, wherein said total quantity controlling means include:

sensor means for detecting a light quantity of the flash tube at every emission time;

means for integrating every light quantity detected by the sensor means; and means for comparing a total light quantity obtained by the integrating means with a predetermined light quantity; and means for determining the number of emission times on the basis of a comparison result of the comparing means.

7. A lighting apparatus comprising:

a flash tube;

a capacitor for storing electric charge to be supplied to the flash tube so that the flash tube emits light;

power supply circuit for charging the capacitor;

plurality of sensors for detecting light quantities in a plurality of wavelength bands respectively;

means for computing color temperature of the flash tube from outputs of the plurality of sensors;

means for designating a color temperature;

means for calculating a difference between the computed color temperature and the designated color temperature;

means for storing a predetermined relationship between a plurality of emission time periods of the flash tube and a plurality of differences between the designate color temperature and computed color temperatures;

means for determining a time period on the basis of the difference calculated by the calculating means and of the relationship stored in the storing means; and means for controlling emission time period of the flash tube in accordance with the time period determined by the determining means.

8. The lighting apparatus of claim 7, further comprising means for determining a charge voltage of the capacitor to control the color temperature of the flash tube.

9. The lighting apparatus of claim 7, wherein said controlling means include:

a trigger circuit for starting to send the electric charge from the capacitor to the flash tube;

an insulated-gate bipolar transistor for controlling a discharge of the capacitor through the flash tube; and a pulse circuit for sending a pulse signal to a gate of the insulated-gate bipolar transistor to control the discharge of the capacitor.

10. The lighting apparatus of claim 9, wherein said pulse circuit includes means for controlling either of a voltage and a width of the pulse signal sent to the gate of the insulated gate bipolar transistor.

11. Color measuring apparatus for measuring color of a sample, comprising:

a flash tube positioned so as to illuminate the sample;

first detecting means for detecting light from the sample illuminated by the flash tube;

means for designating a color temperature;

means for controlling a time period of a light emission of the flash tube on the basis of the designated color temperature and a detected result of the first detecting means; and means for measuring a color of the sample in accordance with the light detected by the first detecting means.

12. Color measuring apparatus of claim 11, further comprising:

a capacitor for storing electric charge to be supplied to the flash tube;

power supply circuit for charging the capacitor;

means for storing a relationship between a plurality of emission time periods of the flash tube and a plurality of color temperatures of the flash tube;

means for calculating a time period on the basis of a predetermined color temperature and of the relationship stored in the storing means; and means for searching a wavelength band where a result obtained by the first detecting means is lower than a result in another wavelength band;

wherein said controlling means include:

means for determining a color temperature which has a larger light quantity in the searched wavelength band than a previous light quantity in the same band; and means for controlling the calculating means to calculate a time period of a next emission with using the determined color temperature to replace the predetermined color temperature.

13. Color measuring apparatus of claim 12, further comprising second detecting means for detecting a quantity of light coming from the flash tube without passing through the sample and without being reflected by the sample, wherein said searching means include means for comparing results of the first detecting means with results of the second detecting means to search a wavelength band where a ratio of the result of the second detecting means against the result of the first detecting means is lower than a ratio in another wavelength band.

14. Color measuring apparatus for measuring color of a sample, comprising:
   a flash tube positioned so as to illuminate the sample;
   means for counting time from previous emission of the flash tube;
   means for storing a relationship between color temperature values of the flash tube and time elapses from previous emission of the flash tube;
   means for controlling the flash tube on the basis of the counted time by the counting means and the relationship stored in the storing means so that the color temperature of the flash tube in a next emission is not affected by the temperature change with time passage for the flash tube;
   means for detecting spectral light from the sample illuminated by the flash tube; and
   means for measuring color of the sample in accordance with the light detected by the detecting means.

* * * * *